United States Patent
Hearn et al.

(10) Patent No.: US 6,169,218 B1
(45) Date of Patent: Jan. 2, 2001

(54) SELECTIVE HYDROGENATION OF HIGHLY UNSATURATED COMPOUNDS IN HYDROCARBON STREAMS

(75) Inventors: Dennis Hearn, Houston; Robert P. Arganbright, Seabrook; Edward M. Jones, Jr., Friendswood; Lawrence A. Smith, Jr., Bellaire; Gary R. Gildert, Houston, all of TX (US)

(73) Assignee: Catalytic Distillation Technologies

( * ) Notice: Under 35 U.S.C. 154(b), the term of this patent shall be extended for 0 days.

(21) Appl. No.: 08/978,123

(22) Filed: Nov. 25, 1997

Related U.S. Application Data (63) Continuation of application No. 08/163,311, filed on Dec. 8, 1993, now abandoned, which is a continuation-in-part of application No. 07/933,753, filed on Aug. 24, 1992, now abandoned, and a continuation-in-part of application No. 08/079,975, filed on Jun. 21, 1993, now abandoned, which is a continuation of application No. 07/833,360, filed on Feb. 10, 1992, now abandoned.

(51) Int. Cl.[7] ................................................ C07C 5/03
(52) U.S. Cl. ..................... 585/260; 585/259; 585/256; 585/261; 585/32; 203/DIG. 6; 208/143; 208/144
(58) Field of Search .................. 585/259, 256, 585/260, 261, 32; 203/DIG. 6; 208/143, 144

(56) References Cited

U.S. PATENT DOCUMENTS

| 2,717,202 | 9/1955 | Bailey | 23/283 |
|---|---|---|---|
| 3,839,486 | 10/1974 | Arganbright | 585/670 |
| 4,215,011 | 7/1980 | Smith | 252/426 |
| 4,221,653 | 9/1980 | Chervenak et al. | 208/8 LE |
| 4,232,177 | 11/1980 | Smith | 585/324 |
| 4,242,530 | 12/1980 | Smith | 585/510 |
| 4,302,356 | 11/1981 | Smith et al. | 252/426 |

(List continued on next page.)

FOREIGN PATENT DOCUMENTS

| 87980 | 9/1983 | (EP) | 581/260 |
|---|---|---|---|
| 835689 | 5/1960 | (GB) | 260/677 H |
| 920012 | 3/1983 | (GB) | 585/260 |

OTHER PUBLICATIONS

Cameron, C, et al "New Processes for upgrading C4 and C5 Olefini Streams " IFP. Aug. 1994.

Heck et al "Catalytic Processes Using $C_4$ Streams For Octane Improvement: Hydro–Isomerization and MTBC ", Paper Presented to Division of Petroleum Chemistry, Inc. ACS Mar. 1980.

Boitiaux, et al "Newest Hydrogenation Catalysts " Hydrocarbon Processing, Mar. 1985, pp. 51–59.

* cited by examiner

Primary Examiner—Walter D. Griffin
Assistant Examiner—Nadine Preisch
(74) Attorney, Agent, or Firm—Kenneth H. Johnson (57) ABSTRACT

A process for the selective hydrogenation of the diolefins and acetylenic compounds in a olefin rich aliphatic hydrocarbon streams is disclosed wherein the selective hydrogenation is carried out at 40 to 300° F. under low hydrogen partial pressure in the range of about 0.1 psi to less than 70 psia at 0 to 350 psig in a distillation column reactor containing a hydrogenation catalyst which serves as a component of a distillation structure, such as supported PdO encased in tubular wire mesh. Essentially no hydrogenation of the olefins occurs.

78 Claims, 4 Drawing Sheets

U.S. PATENT DOCUMENTS

| | | | |
|---|---|---|---|
| 4,307,254 | 12/1981 | Smith et al. | 568/697 |
| 4,336,407 | 6/1982 | Smith | 568/697 |
| 4,361,422 | 11/1982 | Derrien et al. | 44/56 |
| 4,404,124 * | 9/1983 | Johnson et al. | 585/259 |
| 4,439,350 | 3/1984 | Jones | 502/527 |
| 4,443,559 | 4/1984 | Smith et al. | 502/527 |
| 4,482,775 | 11/1984 | Smith | 585/671 |
| 4,504,687 | 3/1985 | Jones | 568/697 |
| 4,533,779 | 8/1985 | Boitiaux et al. | 585/259 |
| 4,536,373 | 8/1985 | Jones | 422/211 |
| 4,547,600 * | 10/1985 | Cosyns et al. | 585/259 |
| 4,740,633 | 4/1988 | Boitiaux et al. | 568/699 |
| 5,087,780 | 2/1992 | Arganbright | 585/260 |
| 5,679,241 * | 10/1997 | Stanley et al. | 208/92 |
| 5,866,734 * | 2/1999 | Flick et al. | 585/220 |
| 5,877,363 * | 3/1999 | Gildert et al. | 585/324 |

SELECTIVE HYDROGENATION OF HIGHLY UNSATURATED COMPOUNDS IN HYDROCARBON STREAMS

This application is a continuation of U.S. Ser. No. 08/163,311 filed Dec. 8, 1993 now abandoned which is a continuation in part of U.S. Ser. No. 07/933,753 filed Aug. 24, 1992 now abandoned and U.S. Ser. No. 08/079,975 filed Jun. 21, 1993 now abandoned which was a continuation of U.S. Ser. No. 07/833,360 filed Feb. 10, 1992 now abandoned.

BACKGROUND OF THE INVENTION

1. Field of the Invention

The present invention relates to the selective hydrogenation of diolefins and acetylenic compounds in a olefin rich stream. More particularly the invention relates to a process utilizing a hydrogenation catalyst in a structure to serve as both the catalyst and as a distillation structure for the simultaneous reaction and separation of the reactants and reaction products.

2. Related Art

Mixed refinery streams often contain a broad spectrum of olefinic compounds. This is especially true of products from either catalytic cracking or thermal cracking processes. These unsaturated compounds comprise ethylene, acetylene, propylene, propadiene, methyl acetylene, butenes, butadiene, amylenes, hexenes etc. Many of these compounds are valuable, especially as feed stocks for chemical products. Ethylene, especially is recovered. Additionally, propylene and the butenes are valuable. However, the olefins having more than one double bond and the acetylenic compounds (having a triple bond) have lesser uses and are detrimental to many of the chemical process in which the single double bond compounds are used, for example polymerization. Over the range of hydrocarbons under consideration, the removal of highly unsaturated compounds is of value as a feed pretreatment, since these compounds have frequently been found to be detrimental in most processing, storage and use of the streams.

The $C_4$ cuts are sources of alkanes and alkenes for paraffin alkylation to produce $C_8$ gasoline blending components and as feeds for ether production.

The $C_5$ refinery cut is valuable as a gasoline blending stock or as source of isoamylene to form an ether by reaction with lower alcohols. Tertiary amyl methyl ether (TAME) is rapidly becoming valuable to refiners as a result of the recently passed Clean Air Act which sets some new limits on gasoline composition. Some of these requirements are (1) to include a certain amount of "oxygenates", such as methyl tertiary butyl ether (MTBE), TAME or ethanol, (2) to reduce the amount of olefins in gasoline, and (3) to reduce the vapor pressure (volatility).

The $C_5$'s in the feed to a TAME unit are contained in a single "light naphtha" cut which contains everything from $C_5$'s through $C_8$'s and higher. This mixture can easily contain 150 to 200 components and thus identification and separation of the products is difficult. Several of the minor components (diolefins) in the feed will react slowly with oxygen during storage to produce "gum" and other undesirable materials. However, these components also react very rapidly in the TAME process to form a yellow, foul smelling gummy material. Thus it is seen to be desirable to remove these components whether the "light naphtha" cut is to be used only for gasoline blending by itself or as feed to a TAME process.

The use of a solid particulate catalyst as part of a distillation structure in a combination distillation column reactor for various reactions is described in U.S. Pat. No.s: (etherification) U.S. Pat. Nos. 4,232,177; 4,307,254; 4,336,407; 4,504,687; 4,918,243; and 4,978,807; (dimerization) U.S. Pat. No. 4,242,530; (hydration) U.S. Pat. No. 4,982,022; (dissociation) U.S. Pat. No. 4,447,668; and (aromatic alkylation) U.S. Pat. Nos. 4,950,834 and 5,019,669. Additionally U.S. Pat. Nos. 4,302,356 and 4,443,559 disclose catalyst structures which are useful as distillation structures.

Hydrogenation is the reaction of hydrogen with a carbon—carbon multiple bond to "saturate" the compound. This reaction has long been known and is usually done at super atmospheric pressures and moderate temperatures using a large excess of hydrogen over a metal catalyst. Among the metals known to catalyze the hydrogenation reaction are platinum, rhenium, cobalt, molybdenum, nickel, tungsten and palladium. Generally, commercial forms of catalyst use supported oxides of these metals. The oxide is reduced to the active form either prior to use with a reducing agent or during use by the hydrogen in the feed. These metals also catalyze other reactions, most notably dehydrogenation at elevated temperatures. Additionally they can promote the reaction of olefinic compounds with themselves or other olefins to produce dimers or oligomers as residence time is increased.

Selective hydrogenation of hydrocarbon compounds has been known for quite some time. Peterson, et al in "The Selective Hydrogenation of Pyrolysis Gasoline" presented to the Petroleum Division of the American Chemical Society in September of 1962, discusses the selective hydrogenation of $C_4$ and higher diolefins. Boitiaux, et al in "Newest Hydrogenation Catalyst", *Hydrocarbon Processing*, March 1985, presents a general, non enabling overview of various uses of hydrogenation catalysts, including selective hydrogenation of a propylene rich stream and other cuts. Conventional liquid phase hydrogenations as presently practiced required high hydrogen partial pressures, usually in excess of 200 psi and more frequently in a range of up to 400 psi or more. In a liquid phase hydrogenation the hydrogen partial pressure is essentially the system pressure.

U.S. Pat. No. 2,717,202 to Bailey discloses a countercurrent process for the hydrogenation of lard carried out in a plurality of independent vertical chamber using a pumped catalyst under undisclosed pressure conditions. U.S. Pat. No. 4,221,653 to Chervenak et al discloses a concurrent hydrogenation for using an ebullating bed at extremely high pressures. UK Patent Specification 835,689 discloses a high pressure, concurrent trickle bed hydrogenation of $C_2$ and $C_3$ fractions to remove acetylenes.

U.S. Pat. No. 5,087,780 to Arganbright disclosed a process for the hydroisomerization of butenes using an alumina supported palladium oxide catalyst arranged in a structure for use as both the catalyst and distillation in a catalytic distillation reactor. The hydrogenation of dienes was also observed under high hydrogen partial pressure, in excess of 70 psia, but not at around 10 psia.

It is an advantage of the present process that the diolefins (dienes) and acetylenic compounds contained within the hydrocarbon stream contacted with the catalyst are converted to olefins or alkanes with very little if any formation of oligomers or little if any saturation of the mono-olefins.

SUMMARY OF THE INVENTION

The present invention comprises feeding a hydrocarbon stream containing highly unsaturated compounds which comprise diolefins and acetylenes along with a hydrogen stream at an effectuating hydrogen partial pressure of at least about 0.1 psia to less than 70 psia, preferably less than 50 psia to a distillation column reactor containing a hydrogenation catalyst which is a component of a distillation structure and selectively hydrogenating a portion of the highly unsaturated compounds. Within the hydrogen partial pressures as defined no more hydrogen than necessary to maintain the catalyst (most likely to reduce the catalyst metal oxide and maintain it in the hydride state) and hydrogenate the highly unsaturated compounds is employed, since the excess hydrogen is usually vented. This preferably is a hydrogen partial pressure in the range of about 0.1 to 10 psia and even more preferably no more than 7 psia. Optimal results have been obtained in the range between 0.5 and 5 psig hydrogen partial pressure.

The hydrocarbon stream typically comprises $C_2$ to $C_9$ aliphatic compounds, which may be narrow cuts or include a range of carbon content. The invention is the discovery that a hydrogenation carried out in a catalytic distillation column requires only a fraction of the hydrogen partial pressure required in the liquid phase processes which are the form of prior commercial operation for this type of stream, but give the same or better result. Thus the capital investment and operating expense for the present hydrogenation are substantially lower than prior commercial operations.

Without limiting the scope of the invention it is proposed that the mechanism that produces the effectiveness of the present process is the condensation of a portion of the vapors in the reaction system, which occludes sufficient hydrogen in the condensed liquid to obtain the requisite intimate contact between the hydrogen and the highly unsaturated compounds in the presence of the catalyst to result in their hydrogenation.

The highly unsaturated compounds may be present in very minor amounts, i.e., a few parts per million up to major amounts, i.e., over 90 weight %. The present invention may be used to remove impurities or to convert commodity amounts of the highly unsaturated compounds into monoolefins or alkanes as desired.

The hydrogen rate must be adjusted at the partial pressure described such that it is sufficient to support the hydrogenation reaction and replace hydrogen lost from the catalyst but kept below that producing hydrogenation of monoolefins which is understood to be the "effectuating hydrogen partial pressure" as that term is used herein.

As can be readily appreciated the amount of the highly unsaturated compound in the hydrocarbon stream is a factor to be considered in selecting the optimum hydrogen partial pressure, since at least a stoichiometric amount of hydrogen must be present in the system to be available for the reaction. When the highly unsaturated compounds are impurities, present in parts per million the lower range of hydrogen partial pressure is a an excess, but it is necessary because of the scarcity of the selective reactant. Also the nature of this reaction between a gas and a liquid and the apparent need to occlude the hydrogen into the liquid makes an excess of hydrogen within the partial pressures a preferred mode of operation.

An additional feature of the process is that a portion of the mono-olefins contained within the stream or produced by the selective hydrogenation of the diolefins may be isomerized to more desirable products. Isomerization can be achieved with the same family of catalysts as used in hydrogenations. Generally the relative rates of reaction for various compounds are in the order of from faster to slower:

(1) hydrogenation of diolefins
(2) isomerization of the mono-olefins
(3) hydrogenation of the mono-olefins.

It has been shown generally that in a stream containing diolefins, the diolefins will be hydrogenated before isomerization occurs. It has also been found that very low total pressures may be used for optimal results in some of the present hydrogenations, preferably in the range of 50 to 150 psig with the same excellent results. Both higher and lower pressures within the broad range may be used may be used with satisfactory results.

DETAILED DESCRIPTION AND PREFERRED EMBODIMENTS

Although the hydrogenation reactions have been described as reversible at elevated temperatures above about 900° F. (See for example the Peterson article cited above) under the temperature conditions employed in the present invention, the hydrogenation is not reversible. In the usual application of a process where the catalyst serves as a distillation component, the equilibrium is constantly disturbed, thus driving the reaction toward completion, that is, the reaction has an increased driving force because the reaction products have been removed and cannot contribute to a reverse reaction (LeChatelier's Principle). In the present process where there is no reversible reaction, no benefit is to be derived by removing the products of the reaction to increase the driving force of the reaction by. Similarly the poor performance of prior vapor phase hydrogenations would not suggest the use of distillation type reaction. Thus, it is unexpected that catalytic distillation would be of benefit for non reversible hydrogenation.

It is believed that in the present reaction catalytic distillation is a benefit first, because the reaction is occurring concurrently with distillation, the initial reaction products and other stream components are removed from the reaction zone as quickly as possible reducing the likelihood of side reactions. Second, because all the components are boiling the temperature of reaction is controlled by the boiling point of the mixture at the system pressure. The heat of reaction simply creates more boil up, but no increase in temperature at a given pressure. As a result, a great deal of control over the rate of reaction and distribution of products can be achieved by regulating the system pressure. Also, adjusting the throughput (residence time =liquid hourly space velocity$^{-1}$) gives further control of product distribution and to a degree control of the side reactions such as oligomerization. A further benefit that this reaction may gain from catalytic distillation is the washing effect that the internal reflux provides to the catalyst thereby reducing polymer build up and coking. Internal reflux may vary over the range of 0.2 to 20 L/D (wt. liquid just below the catalyst bed/wt. distillate) give excellent results, and for the $C_3$–$C_5$ streams usually in the range of 0.5 to 4 L/D.

Quite surprisingly the low hydrogen partial pressure used in the distillation system did not result in the failure of the hydrogenation which would have been expected based on the high hydrogen partial pressure found in the liquid phase systems which are the world wide standard. As observed earlier the phenomenon of condensation which is a constant factor in a distillation is believed to result in the same or better hydrogen availability, as the high pressure in the liquid phase, that is, the hydrogen is introduced into the liquid so that the hydrogenation occurs.

In one embodiment the present invention comprises the selective hydrogenation of acetylenic compounds and di-olefins contained within a propylene rich stream to purify the stream and obtain greater amounts of the propylene. The propylene rich stream is fed to a distillation column reactor into a reaction distillation zone containing a supported palladium oxide catalyst in the form of a catalytic distillation structure. Hydrogen is provided as necessary to support the reaction and, it is believed, to reduce the oxide and maintain it in the hydride state. Previously the hydride state was believed to be the active state, however, the very low amounts of hydrogen present that give excellent results, may indicate otherwise. In any event the state of the catalyst is a matter of theory relating to mechanism, which is not the subject of the present invention. The distillation column reactor is operated at a pressure such that the reaction mixture is boiling in the bed of catalyst. If desired, a bottoms stream containing any higher boiling material may be withdrawn to effectuate a complete separation.

In a $C_3$ embodiment, using the hydrogen partial pressure as recited, the present invention includes a process for the selective hydrogenation of the diolefins and acetylenic compounds contained within a propylene rich stream, comprising the steps of:

(a) feeding (1) a first stream comprising propylene, di-olefins and acetylenic compounds and (2) a second stream containing hydrogen to a distillation column reactor into a feed zone;

(b) concurrently in said distillation column reactor
   (i) contacting said first and second streams in a distillation reaction zone with a hydrogenation catalyst capable of acting as a distillation structure thereby reacting essentially all of said diolefins and acetylenic compounds with said hydrogen to form propylene and other hydrogenated products in a reaction mixture, and
   (ii) separating the propylene contained in said first stream and the propylene formed by the reaction of said diolefins and said acetylenic compounds from said reaction mixture by fractional distillation and (c) withdrawing the separated propylene from step (b) (ii) along with any propane and lighter compounds, including any unreacted hydrogen, from said distillation column reactor as overheads. Optionally the process may include withdrawing any $C_4$ or higher boiling compounds from said distillation column reactor as bottoms. There is no significant loss of propylene from the hydrogenation.

In a $C_5$ embodiment, using the hydrogen partial pressure as recited, the present invention comprises feeding a light naphtha cut containing a mixture of hydrocarbons along with a hydrogen stream to a distillation column reactor containing a hydrogenation catalyst which is a component of a distillation structure and selectively hydrogenating the diolefins contained in the light naphtha. Concurrently the lighter components, including the unreacted hydrogen, are distilled and separated as overheads from the partially hydrogenated light naphtha product. Additionally and concurrently with the selective hydrogenation and distillation, a portion of the $C_5$ mono-olefins are isomerized to a more desirable feed for the production of tertiary amyl methyl ether (TAME) by the reaction of the isoolefin with methanol. Essentially all of the diolefins are converted to mono olefins with very little hydrogenation of the mono-olefins.

In a further embodiment employing the light naphtha the feed is predominately a $C_5$ stream and the light naphtha product is withdrawn as bottoms. The overheads are passed to a condenser in which all of the condensibles are condensed and a portion refluxed to the top of the column. Reflux ratios of 0.5 to 20:1 may be used in the various embodiments.

In another embodiment employing the light naphtha feed, and the hydrogen partial pressure as recited, the feed comprises a broader $C_5$ to $C_8$ stream the $C_5$'s are separated from the $C_6$+ components in the lower section of a distillation column reactor. The $C_6$+ components are withdrawn as a bottoms stream while the $C_5$'s are boiled up into the upper section of the distillation column reactor which contains the catalytic distillation structure which selectively hydrogenates the diolefins. The hydrogenated $C_5$'s are taken overheads along with the excess hydrogen and passed to the condenser in which all of the condensibles are condensed and subsequently separated from the uncondensibles (mostly hydrogen), for example in a reflux drum separator. A portion of the liquid from the separator is returned to the distillation column reactor as reflux and the remainder withdrawn as product which may be directly charged to a TAME unit. If desired a further inert distillation section may be utilized above the catalytic distillation structure with a C5 product side draw below to fractionate out the excess hydrogen along with any other light components such as air, water, etc. which might be troublesome in the downstream TAME unit.

In the light naphtha embodiment the present invention is a process for the selective hydrogenation of diolefins contained in a light naphtha comprising the steps of:

(a) feeding (1) a first stream comprising a light naphtha containing diolefins and (2) a second stream containing hydrogen to a distillation column reactor into a feed zone;

(b) concurrently in said distillation column reactor
   (i) contacting said first and second streams in a distillation reaction zone with a hydrogenation catalyst capable of acting as a distillation structure, thereby reacting essentially all of said diolefins with said hydrogen to form pentenes and other hydrogenated products in a reaction mixture, and
   (ii) operating the pressure of the distillation column reactor such that a portion of the mixture is vaporized by the exothermic heat of reaction;

(c) withdrawing a portion of the liquid from step (b) (ii) from said distillation column reactor as bottoms; and (d) withdrawing the vapors from step (b) (ii) along with any unreacted hydrogen from said distillation column reactor as overheads.

The diolefins contained in the $C_5$ cut are higher boiling than the other compounds and therefore can be concentrated in the catalyst zone while the mono-olefins are isomerized and removed in the upper part of the column. The reactions of the $C_5$'s of interest are:

(1) isoprene (2-methyl butadiene-1,3)+hydrogen to 2-methyl butene-1 and 2-methyl butene-2;

(2) cis- and trans 1,3-pentadienes (cis and trans piperylenes)+hydrogen to pentene-1 and pentene-2;

(3) 3-methyl butene-1 to 2-methyl butene-2 and 2-methyl butene-1;
(4) 2-methyl butene-1 to 2-methyl butene-2;
(5) 2-methyl butene-2 to 2-methyl butene-1; and
(5) 1,3-butadiene to butene-1 and butene-2.

The first two reactions remove the undesirable components while the third is advantageous for feed to a TAME reactor. The 3-methyl butene-1 does not react with methanol to produce TAME over the sulfonic acid catalyst while the two 2-methyl butenes do.

The present invention carries out the method in a catalyst packed column which can be appreciated to contain a vapor phase and some liquid phase as in any distillation. The distillation column reactor is operated at a pressure such that the reaction mixture is boiling in the bed of catalyst. The present process operates at overhead pressure of said distillation column reactor in the range between 0 and 350 psig, preferably 250 or less and temperatures within said distillation reaction zone in the range of 40 to 300° F., preferably 110 to 270° F. at the requisite hydrogen partial pressures. The feed weight hourly space velocity (WHSV), which is herein understood to mean the unit weight of feed per hour entering the reaction distillation column per unit weight of catalyst in the catalytic distillation structures, may vary over a very wide range within the other condition perimeters, e.g. 0.1 to 35. The advantages of utilizing a distillation column reactor in the instant selective hydrogenation process lie in the better selectivity of diolefin to olefin, conservation of heat and the separation by distillation which can remove some undesirable compound, e.g. heavy sulfur contaminants, from the feed prior to exposure to the catalyst and the distillation can concentrate desired components in the catalyst zone.

A "froth level" is preferably maintained throughout the catalyst bed by control of the bottoms and/or overheads withdrawal rate which improves the effectiveness of the catalyst thereby decreasing the height of catalyst needed. As may be appreciated the liquid is boiling and the physical state is actually a froth having a higher density than would be normal in a packed distillation column but less than the liquid without the boiling vapors, as described in U.S. Pat. No. 5,221,441 which is incorporated herein. Basically the froth mode called "liquid phase continuous (LPC)" hereafter is understood to mean that the flow of liquid from the catalytic distillation section has been restricted so that the rising vapor creates a froth. In effect the continuous phase is the liquid rather than the vapor as is usual in a distillation. The result is increased liquid contact with the catalytic material during the distillation and improved selective hydrogenation.

The temperature in the reactor is determined by the boiling point of the liquid mixture present at any given pressure. The temperature in the lower portions of the column will reflect the constitution of the material in that part of the column, which will be higher than the overhead; that is, at constant pressure a change in the temperature of the system indicates a change in the composition in the column. To change the temperature the pressure is changed. Temperature control in the reaction zone is thus effected by a change in pressure; by increasing the pressure, the temperature in the system is increased, and vice versa.

As described the catalytic material employed in the hydrogenation process is in a form to serve as distillation packing. Broadly stated, the catalytic material is a component of a distillation system functioning as both a catalyst and distillation packing, i.e., a packing for a distillation column having both a distillation function and a catalytic function.

The reaction system can be described as heterogenous since the catalyst remains a distinct entity. Any suitable hydrogenation catalyst may be used, for example Group VIII metals of the Periodic Table of Elements as the principal catalytic component, alone or with promoters and modifiers such as palladium/gold, palladium/silver, cobalt/zirconium, nickel preferably deposited on a support such as alumina, fire brick, pumice, carbon, silica, resin or the like.

A preferred catalytic material comprises palladium oxide, preferably 0.1 to 5.0 weight %, supported on an appropriate support medium such as alumina, carbon or silica, e.g., ⅛" alumina extrudates. In a preferred catalytic distillation structure the particulate catalyst material is disposed within a porous plate or screen to contain the catalyst and provide a distillation surfaces, in the form of a wire mesh structure, such as a wire mesh tubular structure or any other similar structure.

A preferred catalyst structure for the present hydrogenation reaction comprising flexible, semi-rigid open mesh tubular material, such as stainless steel wire mesh, filed with a particulate catalytic material in one of several embodiments recently developed in conjunction with the present process.

One new catalyst structure developed for use in hydrogenations is described in U.S. Pat. No. 5,266,546 which is incorporated herein in its entirety. Briefly the new catalyst structure is a catalytic distillation structure comprising flexible, semi-rigid open mesh tubular material, such as stainless steel wire mesh, filed with a particulate catalytic material said tubular material having two ends and having a length in the range of from about one-half to twice the diameter of said tubular material, a first end being sealed together along a first axis to form a first seam and a second end being sealed together along a second axis to form a second seam wherein the plane of the first seam along the axis of said tubular material and the plane of the second seam along the axis of said tubular material bisect each other at an angle of about 15 to 90°.

U.S. Pat. No. 4,242,530 and U.S. Pat. No. 4,443,559 which are incorporated herein, disclose supported catalyst in a plurality of pockets in a cloth belt or wire mesh tubular structures, which is supported in the distillation column reactor by open mesh knitted stainless steel wire by twisting the two together into a helix, which have been used. U.S. Pat. No. 5,348,710, which is incorporated herein, describes several other suitable structures in the prior art and disclosed new structures suitable for this process.

The particulate catalyst material may be a powder, small irregular chunks or fragments, small beads and the like. The particular form of the catalytic material in the structure is not critical, so long as sufficient surface area is provided to allow a reasonable reaction rate. The sizing of catalyst particles can be best determined for each catalytic material (since the porosity or available internal surface area will vary for different material and of course affect the activity of the catalytic material).

For the present hydrogenations the preferred catalysts structures for the packing are those employing the more open structure of permeable plates or screen wire.

Figure 1:
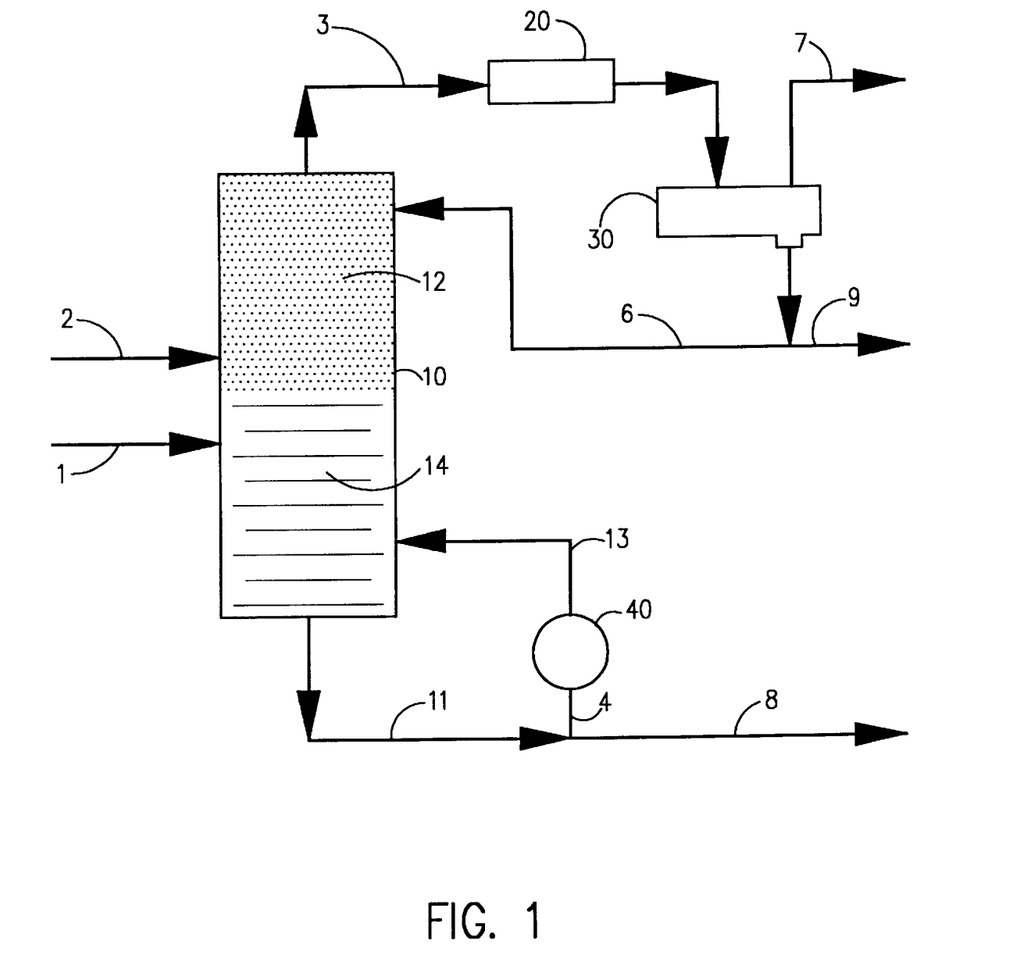
FIG. 1 is a simplified flow diagram of one embodiment of the present invention.

Referring now to FIG. 1 there is shown a simplified flow diagram in schematic of a preferred $C_5$ embodiment. There is shown a distillation column reactor 10 containing a packing of suitable hydrogenation catalyst as part of a distillation structure 12, as in the wire mesh arrangement described above. The column may also have standard distillation structure 14. The light naphtha is fed via line 1 to the distillation column reactor 10 below the catalyst packing.

The hydrogen is fed as a gas via flow line 2 at or near the bottom of the bed of catalyst packing.

The $C_5$ feed and the hydrogen are preferably fed to the distillation column rector separately or they may be mixed prior to feeding. A mixed feed is fed below the catalyst bed or at the lower end of the bed. Hydrogen alone is fed below the catalyst bed and the $C_5$ stream is preferably fed below the bed. Although hydrocarbon is preferably fed below the bed to keep out heavy impurities such as sulfur compounds, it may be fed up to the mid one-third of the bed. The pressure selected is that which maintains the dienes and other highly unsaturated compounds in the catalyst bed while allowing the propylene and lighter to distill overhead.

Heat is added to the bottoms via flow line 4 by circulating through the reboiler 40 and back to the column via flow line 13. After the reaction has started the heat of reaction, which is exothermic, causes additional vaporization of the mixture in the bed. Vapors are taken overhead through flow line 3 and passed to condenser 20 where substantially all of the condensible material is condensed to a temperature of 100° F. The overheads are then passed to reflux drum 30 where the condensed material is collected and separated from uncondensibles, such as the unreacted hydrogen. A portion of the condensed materials collected in the reflux drum are returned to the top of the distillation column reactor 10 via flow line 6. The distillate product, withdrawn through line 9, is a suitable feed for a TAME reactor. The uncondensible material is vented from the reflux drum via flow line 7 and for economy the hydrogen can recycled to the reactor (not shown).

Bottoms product containing essentially no $C_5$ diolefins is withdrawn via flow line 8 and may be sent to gasoline blending as stable gasoline. The process is advantageous because the high heat of hydrogenation is absorbed by the vaporization of part of the liquid, so temperature control is achieved by adjusting the system pressure. All excess hydrogen is stripped from the bottoms product. In the case of $C_5^1$s, the unhydrogenated components are less volatile and tend to stay in the reactor for a longer time assisting in more complete reaction.

Figure 2:
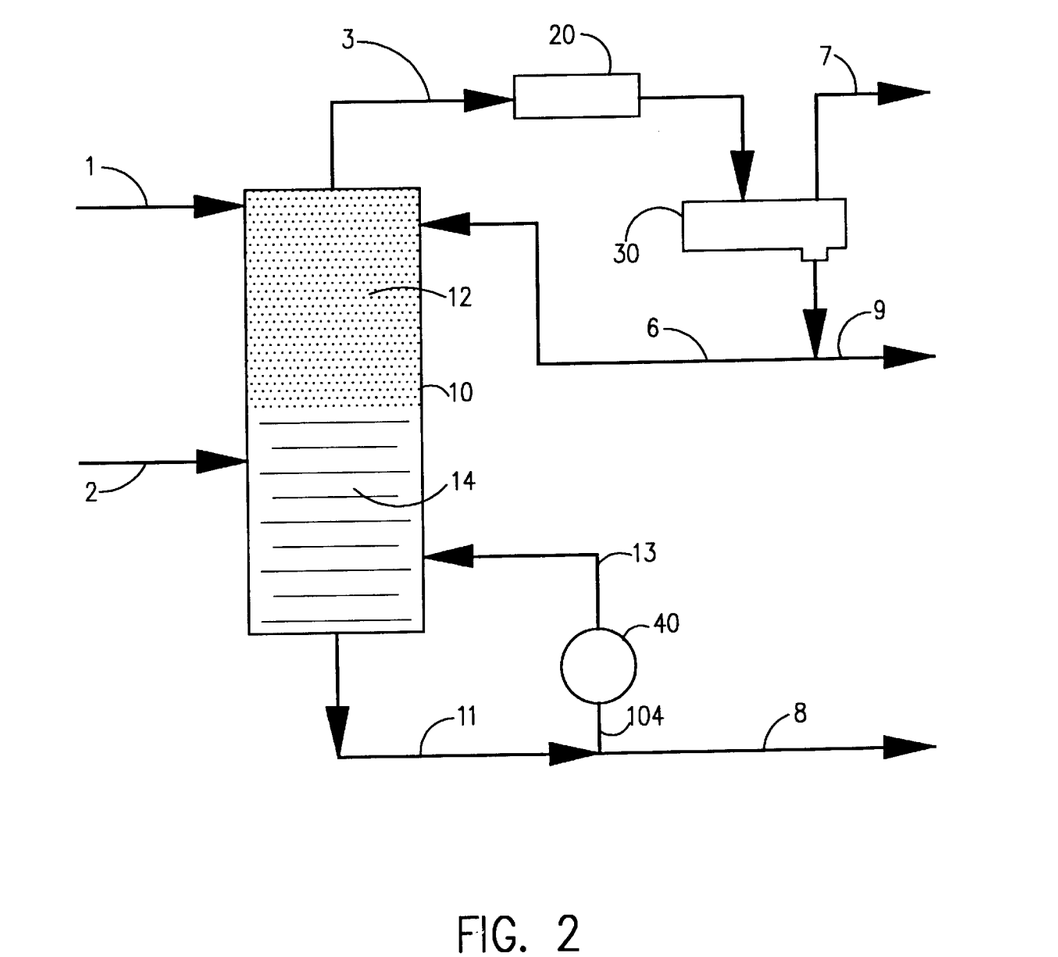
FIG. 2 is a simplified flow diagram of a second embodiment of the present invention.
Figure 3:
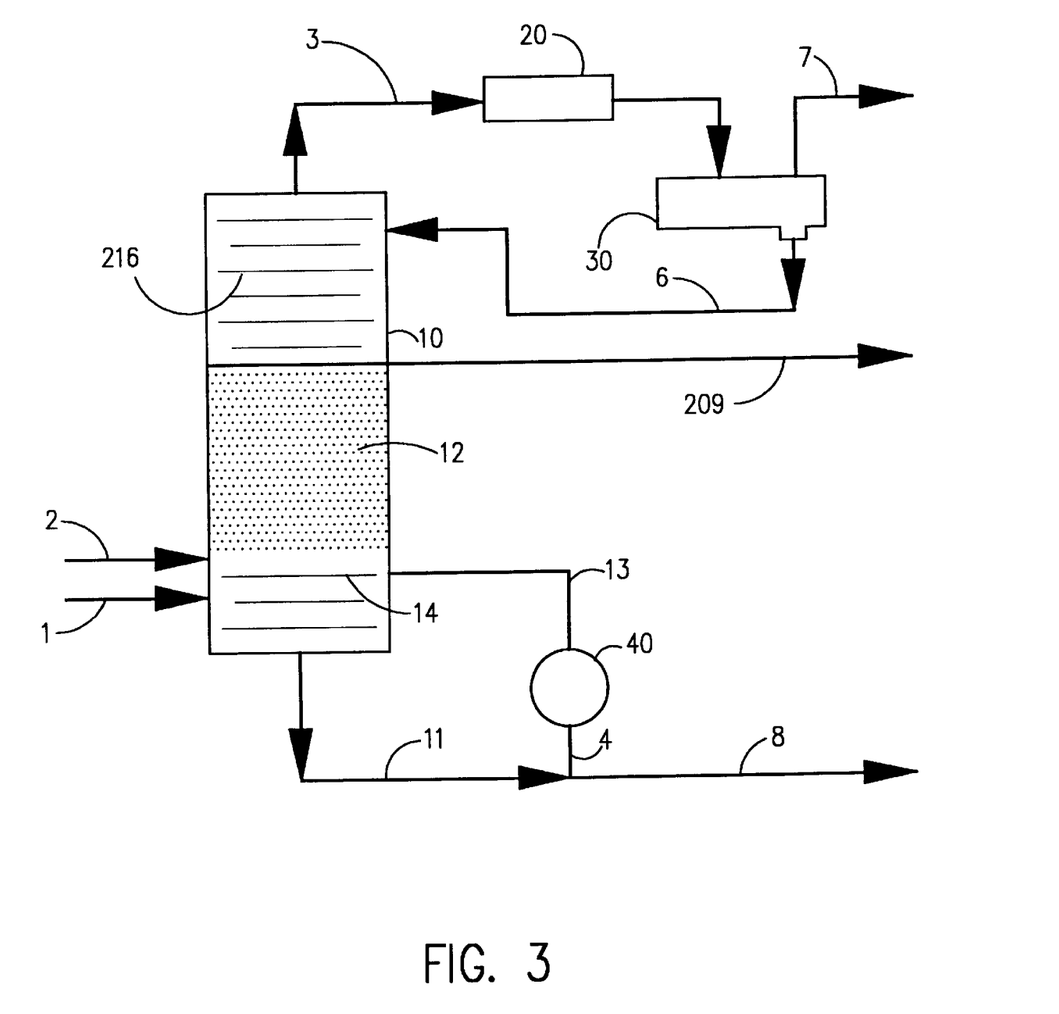
FIG. 3 is a simplified flow diagram of a third embodiment of the present invention.

In FIG. 2 there is shown a second embodiment of the invention wherein the light naphtha is fed to the column 10 above the catalytic distillation structure 12 via flow line 1'. Otherwise the arrangement is identical to FIG. 1. FIG. 3 illustrates a third embodiment wherein the column includes additional conventional distillation structure 216 above the catalytic distillation structure 12 to separate any $C_4$ and lighter material, hydrogen, and other lower boiling components from the $C_5$'s which are withdrawn as side stream via flow line 209.

EXAMPLE 1

In this example the hydrocarbon stream is rich in propylene such as a $C_3$ cut from the gas plant of a fluid catalytic cracking unit or a steam cracker. A typical analysis of such a stream is given in Table II below.

The catalyst is 0.3 wt % PdO on 1/8" $Al_2O_3$ (alumina) extrudates, hydrogenation catalyst, supplied by United Catalysts, Inc. designated as G68F. Typical physical and chemical properties of the catalyst as provided by the manufacturer are as follows:

TABLE I

| Designation | G68F |
|---|---|
| Form | spheres |
| Nominal size | 3 × 6 mesh |
| Pd. wt % | 0.3 |
| Support | High purity alumina |

The catalyst is believed to be the hydride of palladium which is produced during operation.

The hydrogen rate to the reactor must be sufficient to maintain the catalyst in the active form because hydrogen is lost from the catalyst by hydrogenation. The hydrogen rate must be adjusted at the partial pressure described such that it is sufficient to support the hydrogenation reaction and replace hydrogen lost from the catalyst but kept below that required for hydrogenation of propylene and to prevent flooding of the column. Generally the mole ratio of hydrogen to acetylenic compounds in the feed to the fixed bed of the will be about 1.05 to 2.5 preferably 1.4 to 2.0. The presence of hydrogen feed as described herein does not adversely effect the physical operation of the catalytic distillation system.

TABLE II

| Component | Mole Percent |
|---|---|
| Methane | 0.000 |
| Ethylene | 0.000 |
| Ethane | 0.075 |
| Propylene | 82.722 |
| Propane | 11.118 |
| Methyl Acetylene | 2.368 |
| Propadiene | 1.304 |
| Cyclo $C_3$ | 0.048 |
| Isobutane | 0.000 |
| Isobutene | 0.015 |
| Butene-1 | 0.242 |
| Butadiene | 1.529 |
| Normal butane | 0.112 |
| Trans butene-2 | 0.008 |
| Vinyl acetylene | 0.013 |
| Cis butene-2 | 0.000 |
| $C_5$'s and heavier | 0.000 |
| Total | 100.000 |
| Propylene/Propane | 7.440 |

The propylene containing feed and the hydrogen may be fed to the distillation column rector separately or they may be mixed prior to feeding. A mixed feed is fed below the catalyst bed or at the lower end of the bed. Hydrogen alone is fed below the catalyst bed and the $C_3$ stream is preferably fed below the bed. Hydrocarbon fed into the bed can result in some catalyst being deactivated by the impurities. The pressure selected is that which maintains the dienes and acetylenes in the catalyst bed while allowing the propylene and lighter to distill overhead. Any unreacted hydrogen exits overhead with the $C_3$'s.

The pilot unit used was a 1 inch laboratory column fifteen feet in height. The catalyst, 240 grams of 0.3 wt % PdO on 1/8 inch alumina extrudates) was placed in pouches of distillation wire mesh packing to form the catalytic distillation structures described in the U.S. Pat. No. 5,266,546 incorporated herein. The catalytic distillation structures were loaded into the middle ten feet of the column with the lower and upper 2.5 feet filled with inert distillation packing. The propylene rich feed and hydrogen were started to the column and heat added to initiate the reaction. The overhead pressure was maintained at between 240 and 315 psig. In the pilot unit no bottoms were taken, and an equilibrium amount of $C_4$'s +of about 15 vol % was present in the lower section of the column as indicated by a constant temperature of about 140° F. The constant temperature also indicated that no build up of heavier materials occurred as a result of any oligomerization. If there were any residual diene the bottoms temperature would have increased as the heavies built up, thus indicating total selective removal of the dienes and acetylenes. In commercial or larger scale units a bottoms draw would probably be included to effectuate the separation of the $C_4$'s + from the propylene product. Table III below gives the results from the pilot unit run.

TABLE III

| | | | | | | | |
|---|---|---|---|---|---|---|---|
| Time on stream, hrs | 220 | 221 | 237 | 239 | 241 | 335 | 336 |
| Pressure, psig | 315 | 315 | 300 | 280 | 280 | 280 | 280 |
| Btms Temp., ° F. | 140 | 140 | 140 | 140 | 140 | 140 | 140 |
| Feed | | | | | | | |
| Feed Rate lbs/hr (liq.) | 6.0 | 6.0 | 6.0 | 5.9 | 5.9 | 11.0 | 11.0 |
| $H_2$ Rate SCF/hr (gas) | 4.0 | 4.0 | 4.0 | 4.0 | 5.0 | 8.0 | 10.0 |
| $H_2$/Acet. Ratio | 1.452 | 1.451 | 1.468 | 1.493 | 1.867 | 1.602 | 2.002 |
| MA + PD in Feed, Mole % | 3.708 | 3.708 | 3.690 | 3.690 | 3.690 | 3.690 | 3.690 |
| $C_3^=$ | 82.3740 | 82.3740 | 82.3740 | 82.3740 | 82.3740 | 82.3740 | 82.3740 |
| $C_3^=$ + MA + PD | 86.082 | 86.082 | 86.064 | 86.064 | 86.064 | 86.064 | 86.064 |
| dP | 2.7 | 2.7 | 2.6 | 2.6 | 2.7 | 2.6 | 2.6 |
| Overhead Anal, Mole % | | | | | | | |
| Ethane | 0.065 | 0.030 | 0.080 | 0.052 | 0.052 | 0.068 | 0.069 |
| Propylene | 86.460 | 86.184 | 87.221 | 86.379 | 85.583 | 87.355 | 87.421 |
| Propane | 11.717 | 11.304 | 11.074 | 12.041 | 12.353 | 10.687 | 10.957 |
| Methyl acetylene | 0.000 | 0.000 | 0.000 | 0.000 | 0.000 | 0.212 | 0.013 |
| Propadiene | 0.000 | 0.000 | 0.000 | 0.000 | 0.000 | 0.470 | 0.064 |
| Cyclo-$C_3$ | 0.049 | 0.054 | 0.045 | 0.044 | 0.051 | 0.043 | 0.045 |
| Isobutane | 0.000 | 0.000 | 0.000 | 0.000 | 0.000 | 0.000 | 0.000 |
| Isobutene | 0.014 | 0.016 | 0.010 | 0.007 | 0.012 | 0.009 | 0.085 |
| Butene-1 | 0.845 | 1.369 | 0.831 | 0.781 | 0.856 | 0.394 | 0.739 |
| Normal butane | 0.127 | 0.207 | 0.117 | 0.105 | 0.151 | 0.077 | 0.076 |
| Trans butene-2 | 0.544 | 0.950 | 0.472 | 0.466 | 0.600 | 0.116 | 0.292 |
| Vinyl Acetylene | 0.000 | 0.000 | 0.000 | 0.000 | 0.000 | 0.000 | 0.000 |
| Cis butene-2 | 0.185 | 0.327 | 0.144 | 0.155 | 0.237 | 0.031 | 0.056 |
| $C_5$ & heavier | 0.000 | 0.000 | 0.000 | 0.000 | 0.000 | 0.000 | 0.000 |
| % MAPD | 0.000 | 0.000 | 0.000 | 0.000 | 0.000 | 0.682 | 0.077 |

EXAMPLE 2

The catalyst is 0.34 wt % Pd on 3 to 8 mesh $Al_2O_3$ (alumina) spheres, supplied by United Catalysts Inc. designated as G68C. Typical physical and chemical properties of the catalyst as provided by the manufacturer are as follows:

TABLE IV

| | |
|---|---|
| Designation | G68C |
| Form | Sphere |
| Nominal size | 5 × 8 mesh |
| Pd. wt % | 0.3 (0.27–0.33) |
| Support | High purity alumina |

The catalyst is believed to be the hydride of palladium which is produced during operation. The hydrogen rate to the reactor must be sufficient to maintain the catalyst in the active form because hydrogen is lost from the catalyst by hydrogenation. The "effectuating amount of hydrogen" as that term is used herein as regards the $C_5$'s will be at least 1.0 to 1.0 preferably over 2.0 to 1.0, for example about 10:1 moles of hydrogen per mole of diolefin.

Figure 4:
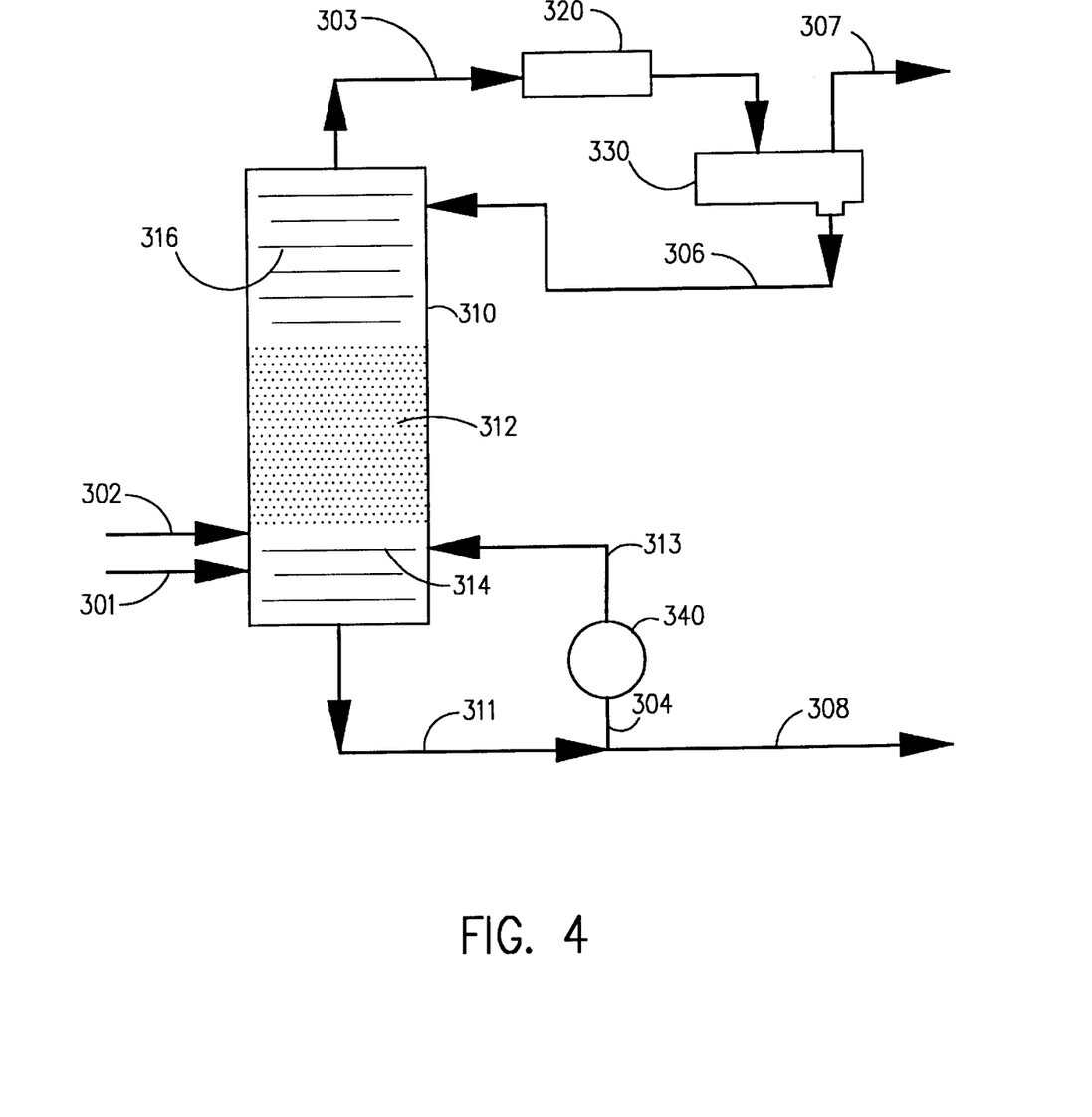
FIG. 4 is a simplified flow diagram of a fourth embodiment of the present invention.

A three inch diameter 30 foot tall steel column 310 with a reboiler 340, condenser 320 and reflux system 330 and 306 is used as shown in FIG. 4. The middle 15 feet are packed with a catalytic distillation structure 312 comprising 0.34 wt % palladium on ⅛ inch alumina spherical catalyst which is contained in the pockets of a fiber glass belt and twisted with stainless steel wire mesh. The column is purged with nitrogen and pressure up to 20 psig. Light naphtha feed which has been prefractionated to remove most of the $C_6$+ material is started to the column via line 301 at 50 lbs/hr. When a bottom level is obtained and the liquid is at the desired level in the column, bottoms draw through line 308 is started and reboiler circulation began through line 304 and 313. Heat is added to the reboiler 340 until vapor is seen at the top of the column as evidenced by a uniform temperature of 130° F. throughout the column. Hydrogen flow is started to the bottom of the column at between 8 to 10 SCFH via line 302.

The pressure on the column is then controlled to maintain a bottoms temperature of about 320° F. and a catalyst bed temperature of about 260° F. The overhead pressure was thus maintained about 200 psig. The overheads are taken via line 303 and partially condensed in condenser 320 and all of the condensibles collected in reflux drum 330 and returned to the top of the column as reflux via line 306. Uncondensibles are vented from the drum via line 307. Liquid bottoms are withdrawn via line 308. The results are shown in TABLE V below in which the feed and bottoms analyses are compared.

TABLE V

| Component, wt % | Feed | Bottoms Product | Change |
|---|---|---|---|
| Lights | 0.073 | 0.000 | −100 |
| Dimethyl ether | 0.003 | 0.002 | −36 |
| isobutane | 0.488 | 0.093 | −81 |
| methanol | 0.058 | 0.000 | −100 |
| Other $C_4$'s | 4.573 | 3.304 | −28 |
| 3-methyl butene-1 | 1.026 | 0.270 | −74 |
| isopentane | 31.974 | 32.066 | 0 |
| pentene-1 | 2.708 | 0.962 | −64 |
| 2-methyl butene-1 | 6.496 | 4.012 | −38 |
| normal pentane | 3.848 | 4.061 | 6 |
| 2-methyl | 0.147 | 0.002 | −99 |

TABLE V-continued

| Component, wt % | Feed | Bottoms Product | Change |
|---|---|---|---|
| butadiene-1,3, trans pentene-2 | 6.995 | 9.066 | 30 |
| Unknown 1 | 0.138 | 0.094 | −32 |
| cis pentene-2 | 3.886 | 3.723 | −4 |
| 2-methyl butene-2 | 11.634 | 14.083 | 21 |
| trans piperylene | 0.142 | 0.002 | −98 |
| cis piperylene | 0.095 | 0.003 | −97 |
| cyclo-$C_5$ | 0.001 | 0.058 | −47 |
| $C_6+$ | 25.603 | 28.198 | 10 |
| Total | 100.000 | 100.000 | |

EXAMPLE 3

During the run of Example 2 the overhead pressure was adjusted to vary the catalyst bed temperature. At lower temperatures the conversion of the diolefins was lower, but the main difference was that the isomerization of the 3-methyl butene-1 was more dramatically affected. Table VI below compares the conversions of the diolefins and 3-methyl butene-1 with the operating temperature.

TABLE VI

| Mid. Temp °F. | OH Press psig | Hrs on STM | Conversion Mole % | | | |
|---|---|---|---|---|---|---|
| | | | isoprene | t-Pip | c-Pip | 3-methyl butene-1 |
| 230 | 130 | 200 | 65 | 57 | 65 | 17 |
| 250 | 145 | 300 | 97 | 95 | 95 | 55 |
| 265 | 200 | 600 | 100 | 99 | 99 | 80 |

EXAMPLE 4

$C_4$ Streams

This set of runs demonstrates the unexpected diene removal from $C_4$ streams at extremely low hydrogen partial pressures. It was also demonstrated that lower total pressures were also suitable. The runs were conducted in two modes. In one mode, conventional distillation, a vapor continuous phase was used. In the other mode, a preferred liquid continuous phase "LPC" mode was used.

The reactor used for Run 1 was a three inch diameter column containing 20 feet of catalyst packing, containing 1 cubic foot of catalytic material (0.5% pd on 8–12 mesh alumina-E144SDU product of Calcicat, Catalyst and Performance Chemicals Division, Mallinckrodt, Inc.), with 4.5 feet of ⅝" steel pall rings above and 15.5 feet of ⅝" steel Pall rings below the catalyst bed. Run 2 used a three inch diameter column containing 20 feet of catalyst packing, containing 1 cubic foot of catalytic material (0.5% pd on 8–12 mesh alumina-E144SDU product of Calcicat, Catalyst and Performance Chemicals Division, Mallinckrodt, Inc.), with 4.5 feet of ⅝" steel pall rings above and 25 feet of demister wire and 50 feet of ⅝" steel Pall rings below the catalyst bed. The catalyst was loaded into tubular one inch wire casings positioned diagonally on demister wire and rolled into a bale of about 3" diameter.

The hydrocarbon is fed to the column below the catalyst. To start up the overhead pressure is set to 120 psig and the reboiler is charged with hydrocarbon fed at about 20 pounds per hour with the reboiler set at 10% which is maintained for 15 minutes at which time the feed rate is adjusted to maintain 50–75% bottoms level until the overhead temperature is within 20 degrees of the bottoms temperature then increase the hydrocarbon feed rate to 100 lb/hr. When the differential pressure reaches 1.0 psi the hydrogen flow is initiated at 15 scfh. Bottoms are heated to a uniform temperature of 1600 F then a mid relux flow is started. The overhead pressure is selected and the reaction distillation is carried out. The $C_4$ hydrocarbon feed conditions and results for each run are set out in TABLES VII and VIII.

Runs carried out in the LPC mode removed all of the dienes whereas conventional distillation left a few parts per million under the same conditions. The internal reflux rate is reported as the ratio of the liquid immediately below the catalyst packing to the distillate (L/D). The data shows the LPC mode to give better diene removal.

TABLE VII

EXAMPLE 4-RUN 1-part 1

HOURS ON LINE 41

CONDITIONS

| | |
|---|---|
| Hydrogen pp,psia | 2.3 |
| Feed Source | Refinery FCC |
| Feed Rate lb/hr | 100 |
| $H_2$ Rate scfh | 15 |
| Pressure, psig | 120 |
| Distillate lb/hr | 93 |
| Internal Reflux Rate | 0.73 |
| Mode | Conventional |

RESULTS

| Analysis | Feed wt % | Overhead wt % | Bottoms wt % | Vent wt % |
|---|---|---|---|---|
| Ethylene | 0.02 | 0.01 | 0.00 | 0.00 |
| Ethane | 0.20 | 0.01 | 0.00 | 0.69 |
| Propylene | 0.27 | 0.22 | 0.00 | 2.61 |
| Propane | 0.48 | 0.44 | 0.00 | 3.34 |
| Isobutane | 31.38 | 32.63 | 0.18 | 31.70 |
| Isobutene | 14.21 | 14.77 | 0.74 | 11.41 |
| Butene-1 | 12.82 | 4.59 | 1.07 | 3.25 |
| 1,3-Butadiene | 0.2788 | 0.0030 | 0.0199 | 0.0000 |
| N-Butane | 9.37 | 10.13 | 8.55 | 4.95 |
| Trans-butene-2 | 17.13 | 24.69 | 25.56 | 11.49 |
| 2,2-Dimethylpropane | 0.00 | 0.00 | 0.08 | |
| Methylcyclopropane | 0.02 | 0.02 | 0.02 | |
| Cis-butene-2 | 12.50 | 12.20 | 53.01 | 4.91 |
| $C'_5$'s | 1.26 | 0.27 | 10.58 | 0.06 |
| Heavies | 0.01 | 0.01 | 0.18 | 0.21 |
| Total | 100.00 | 100.0 | 100.0 | |
| lbs/hr | 100.0 | 93.0 | 5 | 1.8 |
| Temp. °F. | | 155 | 188 | |

COMPONENT SUMMARY

| Component | Feed wt % | Product wt % |
|---|---|---|
| Dienes | 0.28 | 30 ppm |
| Isobutane | 31.4 | 31.0 |
| N-Butenes | 42.5 | 43.0 |
| N-Butane | 9.4 | 10.0 |
| % Butene-1 of total N-Butenes | 30.2 | 10.2 |

EXAMPLE 4-RUN 1-part 2

HOURS ON LINE 102

CONDITIONS

| | |
|---|---|
| Hydrogen pp psia | 1.5 |
| Feed Source | Refinery FCC |

TABLE VII-continued

| | |
|---|---|
| Feed Rate lb/hr | 100 |
| H$_2$ Rate scfh | 10 |
| Pressure, psig | 120 |
| Distillate lb/hr | 93 |
| Internal Reflux Rate | 0.74 |
| Mode | LPC |

RESULTS

| Analysis | Feed wt % | Overhead wt % | Bottoms wt % | Vent wt % |
|---|---|---|---|---|
| Ethylene | 0.02 | 0.01 | 0.00 | 0.00 |
| Ethane | 0.20 | 0.02 | 0.00 | 0.70 |
| Propylene | 0.27 | 0.25 | 0.00 | 2.13 |
| Propane | 0.48 | 0.47 | 0.00 | 2.52 |
| Isobutane | 31.38 | 32.97 | 0.21 | 23.22 |
| Isobutene | 14.21 | 14.82 | 0.81 | 8.18 |
| Butene-1 | 12.82 | 3.67 | 1.15 | 1.92 |
| 1,3-Butadiene | 0.2788 | 0.0000 | 0.0211 | 0.0000 |
| N-Butane | 9.37 | 9.93 | 8.84 | 3.43 |
| Trans-butene-2 | 17.13 | 25.37 | 25.71 | 8.29 |
| 2,2-Dimethylpropane | 0.00 | 0.00 | 0.08 | |
| Methylcyclopropane | 0.02 | 0.02 | 0.02 | |
| Cis-butene-2 | 12.50 | 12.20 | 52.25 | 3.46 |
| C$_5$'s | 1.26 | 0.28 | 10.70 | 0.00 |
| Heavies | 0.01 | 0.00 | 0.20 | 0.00 |
| Total | 100.00 | 100.0 | 100.00 | |
| lbs/hr | 100.0 | 93.1 | 5 | 2.0 |
| Temp. ° F. | | 155 | 188 | |

COMPONENT SUMMARY

| Component | Feed wt % | Product wt % |
|---|---|---|
| Dienes | 0.28 | 0 ppm |
| Isobutane | 31.4 | 31.2 |
| N-Butenes | 42.5 | 42.6 |
| N-Butane | 9.4 | 9.8 |
| % Butene-1 of total N-Butenes | 30.2 | 8.2 |

EXAMPLE 4-RUN 1-part 3

HOURS ON LINE 161

CONDITIONS

| | |
|---|---|
| Hydrogen pp psia | 0.8 |
| Feed Source | Refinery FCC |
| Feed Rate lb/hr | 100 |
| H$_2$ Rate scfh | 5 |
| Pressure, psig | 120 |
| Distillate lb/hr | 93 |
| Internal Reflux Rate | 0.74 |
| Mode | Conventional |

RESULTS

| Anaylsis | Feed wt % | Overhead wt % | Bottoms wt % | Vent wt % |
|---|---|---|---|---|
| Ethylene | 0.02 | 0.01 | 0.00 | 0.00 |
| Ethane | 0.20 | 0.01 | 0.00 | 0.64 |
| Propylene | 0.27 | 0.25 | 0.00 | 1.96 |
| Propane | 0.48 | 0.46 | 0.00 | 2.24 |
| Isobutane | 31.38 | 32.84 | 0.47 | 20.08 |
| Isobutene | 14.21 | 14.87 | 0.87 | 7.12 |
| Butene-1 | 12.82 | 10.32 | 1.20 | 4.26 |
| 1,3-Butadiene | 0.2788 | 0.0262 | 0.0227 | 0.0000 |
| N-Butane | 9.37 | 9.52 | 8.71 | 2.87 |
| Trans-butene-2 | 17.13 | 19.35 | 25.66 | 5.71 |
| 2,2-Dimethylpropane | 0.00 | 0.00 | 0.08 | |
| Methylcyclopropane | 0.02 | 0.02 | 0.02 | |
| Cis-butene-2 | 12.50 | 12.08 | 52.60 | 2.96 |
| C$_5$'s | 1.26 | 0.24 | 10.23 | 0.00 |
| Heavies | 0.01 | 0.00 | 0.12 | 0.00 |
| Total | 100.00 | 100.0 | 100.00 | |

TABLE VII-continued

| lbs/hr | 100.0 | 92.7 | 5 | 2.3 |
|---|---|---|---|---|
| Temp. ° F. | | 156 | 188 | |

COMPONENT SUMMARY

| Component | Feed wt % | Product wt % |
|---|---|---|
| Dienes | 0.28 | 262 ppm |
| Isobutane | 31.4 | 30.9 |
| N-Butenes | 42.5 | 43.0 |
| N-Butane | 9.4 | 9.3 |
| % Butene-1 of total N-Butenes | 30.2 | 22.6 |

EXAMPLE 4-RUN 1-part 4

HOURS ON LINE 198

CONDITIONS

| | |
|---|---|
| Hydrogen pp psia | 1.5 |
| Feed Source | Refinery FCC |
| Feed Rate lb/hr | 100 |
| H$_2$ Rate scfh | 10 |
| Pressure, psig | 120 |
| Distillate lb/hr | 93 |
| Internal Reflux Rate | 0.74 |
| Mode | Conventional |

RESULTS

| Analysis | Feed wt % | Overhead wt % | Bottoms wt % | Vents wt % |
|---|---|---|---|---|
| Ethylene | 0.02 | 0.01 | 0.00 | 0.00 |
| Ethane | 0.20 | 0.01 | 0.02 | 0.64 |
| Propylene | 0.27 | 0.25 | 0.03 | 2.08 |
| Propane | 0.48 | 0.46 | 0.05 | 2.42 |
| Isobutane | 31.38 | 32.97 | 3.92 | 20.74 |
| Isobutene | 14.21 | 14.90 | 2.43 | 7.27 |
| Butene-1 | 12.82 | 7.29 | 2.61 | 3.26 |
| 1,3-Butadiene | 0.2788 | 0.0105 | 0.0509 | 0.0000 |
| N-Butane | 9.37 | 9.64 | 8.81 | 2.90 |
| Trans-butene-2 | 17.13 | 21.91 | 24.64 | 6.32 |
| 2,2-Dimethylpropane | 0.00 | 0.00 | 0.07 | |
| Hethylcyclopropane | 0.02 | 0.02 | 0.02 | |
| Cis-butene-2 | 12.50 | 12.29 | 47.97 | 2.97 |
| C$_5$'s | 1.26 | 0.23 | 9.22 | 0.00 |
| Heavies | 0.01 | 0.01 | 0.17 | 0.00 |
| Total | 100.00 | 100.0 | 100.00 | |
| lbs/hr | 100.0 | 93.0 | 5 | 2.1 |
| Temp. ° F. | | 155 | 188 | |

COMPONENT SUMMARY

| Component | Feed wt % | Product wt % |
|---|---|---|
| Dienes | 0.28 | 105 ppm |
| Isobutane | 31.4 | 31.3 |
| N-Butenes | 42.5 | 42.6 |
| N-Butane | 9.4 | 9.5 |
| % Butene-1 of total N-Butenes | 30.2 | 16.4 |

TABLE VIII

EXAMPLE 4-RUN 2-part 1

HOURS ON LINE 138

CONDITIONS

| | |
|---|---|
| Hydrogen pp psia | 1.5 |
| Feed Source | Refinery FCC |
| Feed Rate lb/hr | 56 |
| H$_2$ Rate scfh | 15 |

TABLE VIII-continued

| | |
|---|---|
| Pressure, psig | 125 |
| Distillate lb/hr | 37 |
| Internal Reflux Rate | 4.72 |
| Mode | LPC |

RESULTS

| Analysis | Feed wt % | Overhead wt % | Bottoms wt % | Vent wt % |
|---|---|---|---|---|
| Ethylene | 0.03 | 0.03 | 0.00 | 0.00 |
| Ethane | 0.22 | 0.11 | 0.00 | 0.14 |
| Propylene | 0.24 | 0.31 | 0.00 | 0.68 |
| Propane | 0.53 | 0.68 | 0.00 | 1.18 |
| Isobutane | 28.17 | 39.45 | 0.01 | 33.16 |
| Isobutene | 15.05 | 21.03 | 0.0032 | 16.91 |
| Butene-1 | 13.91 | 7.81 | 0.01 | 5.99 |
| 1,3-Butadiene | 0.3441 | 0.0000 | 0.0000 | 0.0000 |
| N-Butane | 8.65 | 7.34 | 12.86 | 5.04 |
| Trans-butene-2 | 17.76 | 16.71 | 40.71 | 11.43 |
| 2,2-Dimethylpropane | 0.00 | 0.00 | 0.04 | |
| Methylcyclopropane | 0.02 | 0.01 | 0.03 | |
| Cis-butene-2 | 13.55 | 6.51 | 40.84 | 4.26 |
| $C_5$'s | 1.53 | 0.02 | 5.47 | 0.00 |
| Heavies | 0.00 | 0.00 | 0.01 | 0.05 |
| Total | 100.00 | 100.0 | 100.00 | |
| lbs/hr | 56.0 | 37.1 | 15 | 4.0 |
| Temp. ° F. | | 164 | 182 | |

CONPONENT SUMMARY

| Component | Feed wt % | Product wt % |
|---|---|---|
| Dienes | 0.3 | 0 ppm |
| Isobutane | 28.2 | 28.5 |
| N-Butenes | 45.2 | 43.9 |
| N-Butane | 8.7 | 8.7 |
| % Butene-1 of total N-Butenes | 30.8 | 12.8 |

EXAMPLE 4-RUN 2-part 2

HOURS ON LINE 173

CONDITIONS

| | |
|---|---|
| Hydrogen pp psia | 1.5 |
| Feed Source | Refinery FCC |
| Feed Rate lb/hr | 56 |
| H$_2$ Rate scfh | 15 |
| Pressure, psig | 125 |
| Distillate lb/hr | 32 |
| Internal Reflux Rate | 5.46 |
| Mode | LPC |

RESULTS

| Analysis | Feed wt % | Overhead wt % | Bottoms wt % | Vent wt % |
|---|---|---|---|---|
| Ethylene | 0.03 | 0.03 | 0.00 | 0.02 |
| Ethane | 0.22 | 0.09 | 0.00 | 0.29 |
| Propylene | 0.24 | 0.33 | 0.00 | 0.77 |
| Propane | 0.53 | 0.74 | 0.00 | 2.56 |
| Isobutane | 28.17 | 43.97 | 0.01 | 43.60 |
| Isobutene | 15.05 | 23.39 | 0.0541 | 5.45 |
| Butene-1 | 13.91 | 7.20 | 0.22 | 19.75 |
| 1,3-Butadiene | 0.3441 | 0.0000 | 0.0024 | 0.0000 |
| N-Butane | 8.65 | 5.24 | 15.64 | 3.88 |
| Trans-butene-2 | 17.76 | 13.92 | 42.32 | 8.80 |
| 2,2-Dimethylpropane | 0.00 | 0.00 | 0.03 | |
| Methylcyclopropane | 0.02 | 0.01 | 0.03 | |
| Cis-butene-2 | 13.55 | 5.07 | 37.33 | 3.22 |
| $C_5$'s | 1.53 | 0.00 | 4.35 | 0.00 |
| Heavies | 0.00 | 0.00 | 0.01 | 0.00 |
| Total | 100.00 | 100.0 | 100.00 | |
| lbs/hr | 56.0 | 32.2 | 19 | 4.9 |
| Temp. ° F. | | 164 | 182 | |

TABLE VIII-continued

COMPONENT SUMMARY

| Component | Feed wt % | Product wt % |
|---|---|---|
| Dienes | 0.3 | 0 ppm |
| Isobutane | 28.2 | 29.1 |
| N-Butenes | 45.2 | 44.9 |
| N-Butane | 8.7 | 8.6 |
| % Butene-1 of total N-Butenes | 30.8 | 13.3 |

EXAMPLE 5

Light FCC Naphtha Streams

The same procedures as set out in Example 4 were used, however the catalyst was G68C-1, a 0.4% palladium on 7–12 mesh alumina product of United Catalyst, Inc. Thirty feet of catalyst packing (1.5 cubic foot of catalytic material) prepared as a distillation structure as described in Example 4 was loaded in a three inch column, with 5 feet of ⅝" steel pall rings and 10 feet of open space above and 3 feet of demister wire and 50 feet of ⅝" steel pall rings below. The distillation was conducted to take hydrotreated $C_5$'s overhead and the heavier components as bottoms. The feeds, conditions and results for each of three runs are set out in TABLEs IX-XI.

The results of Run 3 at 74 hours on stream which was carried out at low hydrogen partial pressure and high 20 WHSV were below expectations. By increasing the hydrogen partial pressure to only 4.4 psia at 272 hours on stream in a conventional distillation mode the diene removal was improved 10 fold.

TABLE IX

EXAMPLE 5-RUN 1

HOURS ON LINE 99

CONDITIONS

| | |
|---|---|
| Hydrogen pp, psia | 4.5 |
| Feed Rate, lb/hr | 219 |
| H$_2$ Rate, scfh | 20 |
| Pressure, psig | 125 |
| Distillate, lb/hr | 47 |
| Internal Reflux Rate | 2.11 |
| Mode | LPC |

RESULTS

| Analysis | Feed wt % | Overhead wt % | Bottoms wt % | Vent wt % |
|---|---|---|---|---|
| $C_4$'s | 0.00 | 0.00 | 0.00 | |
| Isobutane | 0.00 | 0.02 | 0.00 | 0.02 |
| Other $C_4$'s | 0.33 | 1.52 | 0.04 | |
| 3-Methyl Butene-1 | 0.28 | 0.27 | 0.06 | |
| Isopentane | 7.40 | 32.40 | 2.32 | 33.23 |
| Pentene-1 | 1.07 | 1.47 | 0.34 | |
| 2-Methyl Butene-1 | 1.81 | 4.09 | 0.60 | |
| N-Pentane | 3.82 | 17.65 | 1.62 | |
| 2-Methyl Butadiene-1,3 | 0.1761 | 0.0000 | 0.0595 | |
| Trans-Pentene-2 | 2.45 | 14.99 | 1.02 | |
| Unknown 1 | 0.02 | 0.04 | 0.02 | |
| Cis-Pentene-2 | 1.36 | 4.86 | 0.59 | 21.62 |
| 2-Methyl Butene-2 | 3.28 | 17.93 | 1.69 | |
| Trans-Piperylene | 0.18 | 0.00 | 0.10 | |
| Cis-Piperylene | 0.06 | 0.00 | 0.04 | |
| Cyclopentene | 0.29 | 0.26 | 0.26 | |

TABLE IX-continued

EXAMPLE 5-RUN 1

| | | | |
|---|---|---|---|
| Unknowns 2 | 5.12 | 4.12 | 11.26 |
| Heavies | 72.36 | 0.38 | 79.97 |
| Total | 100.00 | 100.0 | 100.00 |
| lbs/hr | 218.8 | 47.0 | 171.9 | 0.00 |
| Temp. °F. | | | 256 | 417 |

COMPONENT SUMMARY

| Component | Feed wt % | Product wt % |
|---|---|---|
| Dienes | 1.91 | 17 ppm |
| 2MB1 + 2MB2 | 22.9 | 24.2 |
| Isopentane | 33.4 | 32.5 |
| Pentenes | 22.0 | 22.6 |
| N-Pentane | 17.2 | 18.8 |
| % 3-MB-1 of total Isoamylenes | 5.23 | 1.63 |
| % Pentene-1 of total N-Pentenes | 22.0 | 9.5 |

TABLE X

EXAMPLE 5-RUN 2-page 1

HOURS ON LINE 45

CONDITIONS

| | |
|---|---|
| Hydrogen pp, psia | 4.8 |
| Feed Rate, lb/hr | 217 |
| H₂ Rate, scfh | 20 |
| Pressure, psig | 125 |
| Distillate, lb/hr | 42 |
| Internal Reflux Rate | 2.22 |
| Mode | LPC |

RESULTS

| Analysis | Feed wt % | Overhead wt % | Bottoms wt % | Vent wt % |
|---|---|---|---|---|
| C₄'s | 0.00 | 0.00 | 0.00 | |
| Isobutane | 0.03 | 0.16 | 0.00 | 0.32 |
| Other C₄'s | 1.46 | 7.33 | 0.00 | |
| 3-Methyl Butene-1 | 0.21 | 0.20 | 0.00 | |
| Isopentane | 7.85 | 38.92 | 0.08 | 34.49 |
| Pentene-1 | 0.76 | 1.04 | 0.02 | |
| 2-Methyl Butene-1 | 1.37 | 3.08 | 0.06 | |
| N-Pentane | 3.56 | 13.79 | 0.73 | |
| 2-Methyl Butadiene-1,3 | 0.101 | 0.0000 | 0.0110 | |
| Trans-Pentene-2 | 2.08 | 10.77 | 0.42 | |
| Unknown 1 | 0.02 | 0.04 | 0.01 | |
| Cis-Pentene-2 | 1.15 | 3.50 | 0.29 | 16.97 |
| 2-Methyl Butene-2 | 2.87 | 13.90 | 0.91 | |
| Trans-Piperylene | 0.11 | 0.00 | 0.04 | |
| Cis-Piperylene | 0.04 | 0.00 | 0.01 | |
| Cyclo-C₅ | 0.31 | 0.43 | 0.23 | |
| Unknowns 2 | 6.49 | 6.01 | 6.46 | |
| Heavies | 71.58 | 0.83 | 90.71 | |
| Total | 100.00 | 100.00 | 100.00 | |
| lbs/hr | 217.3 | 41.9 | 175.4 | 0.00 |
| Temp. °F. | | 260 | 406 | |

COMPONENT SUMMARY

| Component | Feed wt % | Product wt % |
|---|---|---|
| Dienes | 1.21 | 0 ppm |
| 2MB1 + 2MB2 | 20.8 | 21.6 |
| Isopentane | 38.4 | 40.3 |
| Pentenes | 19.6 | 18.9 |
| N-Pentane | 17.4 | 17.3 |
| % 3-MB-1 of total Isoamylenes | 4.80 | 0.94 |
| % Pentene-1 of total N-Pentenes | 19.0 | 6.1 |

EXAMPLE 5-RUN 2-page 2

HOURS ON LINE 201

CONDITIONS

| | |
|---|---|
| Hydrogen pp, psia | 2.9 |
| Feed Rate, lb/hr | 219 |
| H₂ Rate, scfh | 20 |
| Pressure, psig | 75 |
| Distillate, lb/hr | 41 |
| Internal Reflux Rate | 2.50 |
| Mode | LPC |

RESULTS

| Analysis | Feed wt % | Overhead wt % | Bottoms wt % | Vent wt % |
|---|---|---|---|---|
| C₄'s | 0.00 | 0.02 | 0.00 | |
| Isobutane | 0.03 | 0.15 | 0.00 | 0.30 |
| Other C₄'s | 1.48 | 6.85 | 0.00 | |
| 3-Methyl Butene-1 | 0.21 | 0.32 | 0.00 | |
| Isopentane | 7.85 | 36.28 | 0.03 | 42.53 |
| Pentene-1 | 0.76 | 1.18 | 0.01 | |
| 2-Methyl Butene-1 | 1.37 | 3.94 | 0.04 | |
| N-Pentane | 3.56 | 15.98 | 0.58 | |
| 2-Methyl Butadiene-1,3 | 0.1013 | 0.0000 | 0.0085 | |
| Trans-Pentene-2 | 2.08 | 12.08 | 0.33 | |
| Unknown 1 | 0.02 | 0.05 | 0.00 | |
| Cis-Pentene-2 | 1.15 | 3.88 | 0.23 | 18.14 |
| 2-Methyl Butene-2 | 2.87 | 13.81 | 0.76 | |
| Trans-Piperylene | 0.11 | 0.00 | 0.04 | |
| Cis-Piperylene | 0.04 | 0.00 | 0.01 | |
| Cyclo-C₅ | 0.31 | 0.42 | 0.20 | |
| Unknowns 2 | 6.49 | 4.49 | 6.35 | |
| Heavies | 71.58 | 0.54 | 91.42 | |
| Total | 100.00 | 100.00 | 100.00 | |
| lbs/hr | 219.0 | 41.0 | 175.7 | 2.6 |
| Temp. °F. | | 212 | 359 | |

COMPONENT SUMMARY

| Component | Feed wt % | Product wt % |
|---|---|---|
| Dienes | 1.21 | 0 ppm |
| 2MB1 + 2MB2 | 20.8 | 20.9 |
| Isopentane | 38.4 | 38.6 |
| Pentenes | 19.6 | 20.5 |
| N-Pentane | 17.4 | 18.2 |
| % 3-MB-1 of total Isoamylenes | 4.80 | 1.50 |
| % Pentene-1 of total N-Pentenes | 19.0 | 6.0 |

TABLE XI

EXAMPLE 5-RUN 3-page 1

HOURS ON LINE 44

CONDITIONS

| | |
|---|---|
| Hydrogen pp, psia | 2.7 |
| Feed Rate, lb/hr | 295 |
| H₂ Rate, scfh | 20 |
| Pressure, psig | 100 |
| Distillate, lb/hr | 55 |

TABLE XI-continued

| | |
|---|---|
| Internal Reflux Rate | 2.65 |
| Mode | LPC |

RESULTS

| Analysis | Feed wt % | Overhead wt % | Bottoms wt % | Vent wt % |
|---|---|---|---|---|
| $C_4$'s | 0.02 | 0.07 | 0.00 | |
| Isobutane | 0.07 | 0.27 | 0.00 | 0.49 |
| Other $C_4$'s | 1.41 | 0.00 | 0.00 | |
| 3-Methyl Butene-1 | 0.25 | 0.73 | 0.00 | |
| Isopentane | 8.66 | 36.35 | 0.20 | 26.57 |
| Pentene-1 | 0.87 | 2.09 | 0.02 | |
| 2-Methyl Butene-1 | 1.83 | 6.60 | 0.05 | |
| N-Pentane | 1.51 | 6.42 | 0.12 | |
| 2-Methyl Butadiene-1,3 | 0.0537 | 0.0024 | 0.0000 | |
| Trans-Pentene-2 | 2.58 | 13.00 | 0.21 | |
| Unknown 1 | 0.03 | 0.07 | 0.02 | |
| Cis-Pentene-2 | 1.42 | 5.13 | 0.22 | 28.45 |
| 2-Methyl Butene-2 | 3.93 | 15.45 | 1.12 | |
| Trans-Piperylene | 0.06 | 0.00 | 0.02 | |
| Cis-Piperylene | 0.03 | 0.00 | 0.01 | |
| Cyclo-$C_5$ | 0.06 | 0.05 | 0.04 | |
| Unknowns 2 | 7.50 | 6.65 | 7.69 | |
| Heavies | 69.71 | 7.12 | 90.28 | |
| Total | 100.00 | 100.00 | 100.00 | |
| lbs/hr | 294.9 | 55.0 | 236.9 | 3.1 |
| Temp. ° F. | | 240 | 388 | |

COMPONENT SUMMARY

| Component | Feed wt % | Product wt % |
|---|---|---|
| Dienes | 0.68 | 53 ppm |
| 2MB1 + 2MB2 | 27.1 | 27.7 |
| Isopentane | 40.7 | 39.7 |
| Pentenes | 22.9 | 24.4 |
| N-Pentane | 7.1 | 7.1 |
| % 3-MB-1 of total Isoamylenes | 4.23 | 2.61 |
| % Pentene-1 of total N-Pentenes | 17.8 | 9.2 |

EXAMPLE 5-RUN 3-page 2

HOURS ON LINE 74

CONDITIONS

| | |
|---|---|
| Hydrogen pp, psia | 1.5 |
| Feed Rate, lb/hr | 295 |
| $H_2$ Rate, scfh | 10 |
| Pressure, psig | 100 |
| Distillate, lb/hr | 52 |
| Internal Reflux Rate | 2.56 |
| Mode | LPC |

RESULTS

| Analysis | Feed wt % | Overhead wt % | Bottoms wt % | Vent wt % |
|---|---|---|---|---|
| $C_4$'s | 0.02 | 0.08 | 0.00 | |
| Isobutane | 0.07 | 0.29 | 0.00 | 0.68 |
| Other $C_4$'s | 1.41 | 6.44 | 0.00 | |
| 3-Methyl Butene-1 | 0.25 | 1.13 | 0.00 | |
| Isopentane | 8.66 | 39.14 | 0.20 | 32.86 |
| Pentene-1 | 0.87 | 3.65 | 0.02 | |
| 2-Methyl Butene-1 | 1.83 | 8.35 | 0.05 | |
| N-Pentane | 1.51 | 5.84 | 0.12 | |
| 2-Methyl Butadiene-1,3 | 0.0537 | 0.0417 | 0.0000 | |
| Trans-Pentene-2 | 2.58 | 10.45 | 0.21 | |
| Unknown 1 | 0.03 | 0.07 | 0.02 | |
| Cis-Pentene-2 | 1.42 | 5.11 | 0.22 | 0.00 |
| 2-Methyl Butene-2 | 3.93 | 13.09 | 1.12 | |
| Trans-Piperylene | 0.06 | 0.03 | 0.02 | |
| Cis-Piperylene | 0.03 | 0.05 | 0.01 | |
| Cyclo-$C_5$ | 0.06 | 0.06 | 0.04 | |
| Unknowns 2 | 7.50 | 5.29 | 7.69 | |
| Heavies | 69.71 | 0.90 | 90.28% | |
| Total | 100.00 | 100.00 | 100.00 | |
| lbs/hr | 295.1 | 52.0 | 241.2 | 2.0 |
| Temp. ° F. | | 236 | 383 | |

COMPONENT SUMMARY

| Component | Feed wt % | Product wt % |
|---|---|---|
| Dienes | 0.68 | 1263 ppm |
| 2MB1 + 2MB2 | 27.1 | 27.5 |
| Isopentane | 40.7 | 42.4 |
| Pentenes | 22.9 | 21.9 |
| N-Pentane | 7.1 | 6.5 |
| % 3-MB-1 of total Isoamylenes | 4.23 | 4.02 |
| % Pentene-1 of total N-Pentenes | 17.8 | 17.6 |

EXAMPLE 5-RUN 3-page 3

HOURS ON LINE 272

CONDITIONS

| | |
|---|---|
| Hydrogen pp, psia | 4.4 |
| Feed Rate, lb/hr | 295 |
| $H_2$ Rate, scfh | 30 |
| Pressure, psig | 100 |
| Distillate, lb/hr | 53 |
| Internal Reflux Rate | 2.43 |
| Mode | Conventional |

RESULTS

| Analysis | Feed wt % | Overhead wt % | Bottoms wt % | Vent wt % |
|---|---|---|---|---|
| $C_4$'s | 0.02 | 0.08 | 0.00 | |
| Isobutane | 0.07 | 1.03 | 0.00 | 1.58 |
| Other $C_4$'s | 1.41 | 11.21 | 0.00 | |
| 3-Methyl Butene-1 | 0.25 | 0.91 | 0.00 | |
| Isopentane | 8.66 | 42.05 | 0.60 | 26.14 |
| Pentene-1 | 0.87 | 2.11 | 0.14 | |
| 2-Methyl Butene-1 | 1.83 | 6.24 | 0.36 | |
| N-Pentane | 1.51 | 5.06 | 0.63 | |
| 2-Methyl Butadiene-1,3 | 0.0537 | 0.0057 | 0.0000 | |
| Trans-Pentene-2 | 2.58 | 9.32 | 0.98 | |
| Unknown 1 | 0.03 | 0.06 | 0.02 | |
| Cis-Pentene-2 | 1.42 | 3.98 | 0.60 | 18.29 |
| 2-Methyl Butene-2 | 3.93 | 11.56 | 1.87 | |
| Trans-Piperylene | 0.06 | 0.00 | 0.03 | |
| Cis-Piperylene | 0.03 | 0.01 | 0.01 | |
| Cyclo-$C_5$ | 0.06 | 0.04 | 0.04 | |
| Unknowns 2 | 7.50 | 5.29 | 13.06 | |
| Heavies | 69.71 | 1.11 | 81.65 | |
| Total | 100.00 | 100.00 | 100.00 | |
| lbs/hr | 295.0 | 53.0 | 238.1 | 4.00 |
| Temp. ° F. | | 233 | 369 | |

COMPONENT SUMMARY

| Component | Feed wt % | Product wt % |
|---|---|---|
| Dienes | 0.68 | 126 ppm |
| 2MB1 + 2MB2 | 27.1 | 25.7 |
| Isopentane | 40.7 | 43.1 |
| Pentenes | 22.9 | 22.6 |
| N-Pentane | 7.1 | 7.3 |
| % 3-MB-1 of total Isoamylenes | 4.23 | 3.17 |
| % Pentene-1 of total N-Pentenes | 17.8 | 11.2 |

EXAMPLE 6
$C_3$ Streams

The same procedures as set out in Example 4 were used, however the catalyst in Run 1 was G68C, a 0.3% palladium on 3–6 mesh alumina product of United Catalyst, Inc. Twenty feet of catalyst packing (1.0 cubic foot of catalytic material) prepared as distillation structures as described in U.S. Pat. No. 5,266,546, which are tubular wire mesh about 2" long with 2" diameter having the ends sealed at 90° to each other. The catalyst packing was loaded in a three inch column, with 5 feet of ⅝" steel pall rings and 10 feet of open space above and 3 feet of demister wire and 50 feet of ⅝" steel pall rings below. The same structures and column was used in Run 2, but the catalyst was United Catalyst G68H (0.3% Pd and 0.3% Ag on alumina)

The distillation was conducted to take hydrotreated $C_5$'s overhead and the heavier components as bottoms. The feeds, conditions and results for each of three runs are set out in TABLEs XII and XIII.

TABLE XII

EXAMPLE 6-RUN 1

HOURS ON LINE 213

CONDITIONS

| | |
|---|---|
| Hydrogen pp, psia | 6.4 |
| Feed Rate, lb/hr | 90 |
| H₂ Rate, scfh | 34 |
| Pressure, psig | 250 |
| Distillate, lb/hr | 82 |
| Internal Reflux Ratio | 0.88 |
| Mode | LPC |

RESULTS

| Analysis | Feed wt % | Overhead wt % | Bottoms wt % | Vent wt % |
|---|---|---|---|---|
| Methane | 0.00 | 0.00 | 0.00 | 0.06 |
| Ethylene | 0.00 | 0.00 | 0.00 | 0.45 |
| Ethane | 0.05 | 0.03 | 0.00 | |
| Propene | 85.43 | 88.88 | 22.85 | 78.94 |
| Propane | 9..93 | 11.02 | 8.81 | 7.20 |
| Methylacetylene | 1.99 | 0.0000 | 7.66 | |
| Propadiene | 0.81 | 0.0000 | 5.45 | |
| Cyclopropane | 0.05 | 0.04 | 0.34 | |
| Isobutane | 0.00 | 0.00 | 0.10 | |
| Isobutene | 0.01 | 0.00 | 0.27 | |
| Butene-1 | 0.21 | 0.00 | 6.30 | 0.13 |
| Butadiene | 1.37 | 0.00 | 25.59 | |
| N-butane | 0.00 | 0.00 | 2.56 | |
| Vinylacetylene | 0.00 | 0.00 | 0.22 | |
| Trans-butene-2 | 0.01 | 0.00 | 2.34 | |
| Cis-butene-2 | 0.01 | 0.00 | 1.12 | |
| $C_5$'s | 0.04 | 0.00 | 0.75 | 0.04 |
| $C_6$'s | 0.00 | 0.00 | 13.51 | |
| Heavies | 0.00 | 0.00 | 0.01 | 0.05 |
| Total | 100.00 | 100.0 | 100.00 | |
| lbs/hr | 56.0 | 37.1 | 15 | 4.1 |
| Temp. ° F. | | 113 | 216 | |

COMPONENT SUMMARY

| Component | Feed wt % | Product wt % |
|---|---|---|
| Dienes | 4.2 | 0 ppm |
| Propylene | 85.4 | 85.8 |

TABLE XII-continued

EXAMPLE 6-RUN 1

| | | |
|---|---|---|
| Propane | 9.9 | 10.8 |
| $C_6$ | 0.06 | 0.65 |

TABLE XIII

EXAMPLE 6-RUN 2

HOURS ON LINE 152

CONDITIONS

| | |
|---|---|
| Hydrogen pp, psia | 5.2 |
| Feed Rate, lb/hr | 90 |
| H₂ Rate, scfh | 34 |
| Pressure, psig | 250 |
| Distillate, lb/hr | 84 |
| Internal Reflux Ratio | 1.27 |
| Mode | LPC |

RESULTS

| Analysis | Feed wt % | Overhead wt % | Bottoms wt % | Vent wt % |
|---|---|---|---|---|
| Methane | 0.00 | 0.00 | 0.00 | 0.01 |
| Ethylene | 0.00 | 0.00 | 0.00 | 0.54 |
| Ethane | 0.05 | 0.03 | 0.00 | |
| Propene | 85.43 | 88.94 | 22.17 | 74.14 |
| Propane | 9.93 | 10.12 | 10.13 | 6.47 |
| Methylacetylene | 1.99 | 0.0000 | 8.70 | |
| Propadiene | 0.81 | 0.0000 | 5.90 | |
| Cyclopropane | 0.05 | 0.03 | 0.43 | |
| Isobutane | 0.00 | 0.00 | 0.39 | |
| Isobutene | 0.01 | 0.00 | 0.34 | |
| Butene-1 | 0.21 | 0.00 | 6.08 | 0.13 |
| Butadiene | 1.37 | 0.00 | 30.57 | |
| N-butane | 0.00 | 0.00 | 3.02 | |
| Vinylacetylene | 0.00 | 0.00 | 0.25 | |
| Trans-butene-2 | 0.01 | 0.00 | 0.70 | |
| Cis-butene-2 | 0.01 | 0.00 | 0.22 | |
| $C_5$'s | 0.04 | 0.00 | 0.83 | 0.04 |
| $C_6$'s | 0.00 | 0.00 | 8.76 | |
| Heavies | 0.05 | 0.02 | 1.52 | |
| Total | 100.00 | 100.0 | 100.00 | |
| lbs/hr | 90.0 | 83.9 | 3.5 | 2.8 |
| Temp. ° F. | | 113 | 171 | |

COMPONENT SUMMARY

| Component | Feed wt % | Product wt % |
|---|---|---|
| Dienes | 4.2 | 0 ppm |
| Propylene | 85.4 | 86.1 |
| Propane | 9.9 | 10.0 |
| $C_6$ | 0.06 | 0.42 |

The invention claimed is:

1. A process for the selective hydrogenation of highly unsaturated compounds comprising the steps of:
   (a) feeding (1) a hydrocarbon stream containing highly unsaturated compounds which comprise diolefins and acetylenes and (2) a stream containing hydrogen to a distillation column reactor;
   (b) concurrently in said distillation column reactor at an effectuating hydrogen partial pressure hydrogen partial pressure in the range of at least about 0.1 psi to less than 70 psi:
     (i) contacting said streams in a distillation reaction zone with a hydrogenation catalyst prepared in a form to act as a distillation structure thereby to selectively hydrogenate a portion of said highly unsaturated compounds with said hydrogen to form less unsaturated hydrocarbons in a reaction mixture in a mixed vapor/liquid phase, and (ii) separating olefins produced by said selective hydrogenation from said reaction mixture by fractional distillation in said distillation structure while providing for condensing of a portion of said hydrocarbons comprising said olefins and highly unsaturated hydrocarbon compounds.

2. The process according to claim 1 wherein said hydrocarbon stream comprises aliphatic compounds having three to nine carbon atoms.

3. The process according to claim 1 wherein said hydrocarbon stream comprises a major amount of normal olefins which are recovered as products from said hydrogenation.

4. The process according to claim 1 wherein said hydrocarbon has a WHSV in the range of 0.1 to 35.

5. The process according to claim 2 wherein the overhead pressure is in the range of 0 to 350 psig.

6. The process according to claim 1 wherein the hydrogen partial pressure is less than 50 psia.

7. The process according to claim 6 wherein the hydrogen partial pressure is less than 10 psia.

8. The process according to claim 7 wherein the hydrogen partial pressure is less than 7 psia.

9. The process according to claim 5 wherein said hydrogen partial pressure is less than 50 psia.

10. The process according to claim 9 wherein the hydrogen partial pressures is less than 10 psia.

11. The process according to claim 10 wherein the hydrogen partial pressure is less than 7 psia.

12. The process according to claim 1 wherein hydrogenation catalyst comprises a Group VIII metal or metal compound as the principal catalytic component.

13. The process according to claim 12 wherein said catalyst comprises Pd.

14. The process according to claim 5 wherein said overhead pressure is in the range of 50 to 150 psia.

15. The process according to claim 1 comprising the steps of:

(a) feeding (1) a first stream comprising olefins, diolefins and acetylenic hydrocarbon compounds and (2) a second stream containing hydrogen to a distillation column reactor into a feed zone;

(b) concurrently in said distillation column reactor under a hydrogen partial pressure of about 0.1 psi to less than 50 psi:

(i) contacting said streams in a distillation reaction zone with a hydrogenation catalyst prepared in a form to act as a distillation structure thereby reacting essentially all of said di-olefins and acetylenic compounds with said hydrogen to form less unsaturated hydrocarbons in a reaction mixture in a partial liquid phase, and (ii) separating the olefins contained in said first stream and any olefins produced by said hydrogenation from said reaction mixture by fractional distillation while providing for condensing of a portion of said hydrocarbons comprising said olefins, di-olefins and acetylenic hydrocarbon compounds in said distillation reaction zone.

16. The process according to claim 15 wherein said first stream is fed at or below the lower end of said distillation reaction zone.

17. The process according to claim 15 wherein said streams are fed separately to said distillation column reactor.

18. The process according to claim 15 wherein said first and second streams are mixed prior to entry into said distillation column reactor.

19. The process according to claim 15 wherein said hydrocarbon stream comprises aliphatic compounds having three to nine carbon atoms.

20. The process according to claim 19 wherein said hydrocarbon stream comprises a $C_3$ fraction.

21. The process according to claim 19 wherein said hydrocarbon stream comprises a $C_4$ cut.

22. The process according to claim 19 wherein said hydrocarbon stream comprises a $C_5$ cut.

23. The process according to claim 19 wherein said hydrocarbon stream comprises a $C_6$ cut.

24. The process according to claim 19 wherein said first and second streams are combined before feeding to said distillation column reactor.

25. The process according to claim 15 wherein hydrogenation catalyst comprises a Group VIII metal or metal compound as the principal catalytic component.

26. The process according to claim 25 wherein said hydrogenation catalyst comprises 0.1 to 5.0 wt % palladium oxide on alumina extrudates.

27. The process according to claim 15 wherein the overhead pressure of said distillation column reactor is between 240 and 315 psig.

28. The process according to claim 27 wherein said first stream comprises propylene.

29. The process according to claim 15 wherein said distillation structure comprises flexible, semi-rigid open mesh tubular material wire mesh, filled with a particulate hydrogenation catalytic material.

30. The process according to claim 15 further comprising step (c) withdrawing the separated olefins from step (b) (ii) along with any unreacted hydrogen and alkanes, from said distillation column reactor as overheads.

31. The process according to claim 15 wherein said distillation column reactor operates at overhead pressure of in the range between 0 and 250 psig.

32. The process according to claim 31 wherein said pressure is in the range of 50 to 150 psig.

33. The process according to claim 15 wherein temperatures within said distillation reaction zone are in the range of 40 to 300° F.

34. The process according to claim 33 wherein temperatures within said distillation reaction zone are in the range of 110 to 270° F.

35. The process according to claim 15 wherein substantially all of said di-olefins and acetylenic compounds are eliminated from said hydrocarbon stream.

36. The process according to claim 15 wherein the first stream has a WHSV in the range of 0.1 to 35.

37. The process according to claim 16 wherein hydrogenation catalyst comprises a Group VIII metal or metal compound as the principal catalytic component.

38. The process according to claim 37 wherein said hydrogenation catalyst comprises 0.1 to 5.0 wt % palladium oxide on alumina extrudates.

39. The process according to claim 37 wherein said distillation column reactor operates at overhead pressure of in the range between 0 and 250 psig.

40. The process according to claim 39 wherein temperatures within said distillation reaction zone are in the range of 40 to 300° F.

41. The process according to claim 40 wherein said pressure is in the range of 50 to 150 psig.

42. The process according to claim 41 wherein temperatures within said distillation reaction zone are in the range of 110 to 270° F.

43. The process according to claim 42 wherein the hydrogen partial pressure is in the range of 0.1 to 10 psia.

44. The process according to claim 43 wherein there is internal reflux in the range of 0.5 to 5 L/D.

45. The process according to claim 15 wherein substantially all of the highly unsaturated compounds are hydrogenated.

46. The process according to claim 1 wherein an overhead fraction containing condensible hydrocarbons is removed from said distillation column reactor, substantially all of the condensible hydrocarbons being condensed and returned to said distillation column reactor as reflux.

47. The process according to claim 13 wherein said catalyst contains silver.

48. The process according to claim 38 wherein said catalyst contains silver.

49. A process for the selective hydrogenation of highly unsaturated compounds comprising the steps of:
 (a) feeding (1) a hydrocarbon stream containing highly unsaturated compounds which comprise diolefins and (2) a stream containing hydrogen to a distillation column reactor;
 (b) concurrently in said distillation column reactor at an effectuating hydrogen partial pressure hydrogen partial pressure in the range of at least about 0.1 psi to less than 70 psi:
  (i) contacting said streams in a distillation reaction zone with a hydrogenation catalyst prepared in a form to act as a distillation structure thereby to selectively hydrogenate a portion of said highly unsaturated compounds with said hydrogen to form less unsaturated hydrocarbons in a reaction mixture in a mixed vapor/liquid phase, and
  (ii) separating olefins produced by said selective hydrogenation from said reaction mixture by fractional distillation in said distillation structure while providing for condensing of a portion of said hydrocarbons comprising said olefins and highly unsaturated hydrocarbon compounds.

50. The process according to claim 47 wherein said hydrocarbon stream comprises aliphatic compounds having three to nine carbon atoms.

51. The process according to claim 47 wherein said hydrocarbon stream comprises a major amount of normal olefins which are recovered as products from said hydrogenation.

52. The process according to claim 49 wherein said hydrocarbon has a WHSV in the range of 0.1 to 35.

53. The process according to claim 50 wherein the overhead pressure is in the range of 0 to 350 psig.

54. The process according to claim 49 wherein the hydrogen partial pressure is less than 50 psia.

55. The process according to claim 54 wherein the hydrogen partial pressure is less than 10 psia.

56. The process according to claim 54 wherein the hydrogen partial pressure is less than 7 psia.

57. The process according to claim 53 wherein said hydrogen partial pressure is less than 50 psia.

58. The process according to claim 57 wherein the hydrogen partial pressures is less than 10 psia.

59. The process according to claim 58 wherein the hydrogen partial pressure is less than 7 psia.

60. The process according to claim 49 wherein hydrogenation catalyst comprises a Group VIII metal or metal compound as the principal catalytic component.

61. The process according to claim 60 wherein said catalyst comprises Pd.

62. The process according to claim 53 wherein said overhead pressure is in the range of 50 to 150 psia.

63. The process according to claim 61 wherein said catalyst contains silver.

64. A process for the selective hydrogenation of highly unsaturated compounds comprising the steps of:
 (a) feeding (1) a hydrocarbon stream containing highly unsaturated compounds which comprise acetylenes and (2) a stream containing hydrogen to a distillation column reactor;
 (b) concurrently in said distillation column reactor at an effectuating hydrogen partial pressure hydrogen partial pressure in the range of at least about 0.1 psi to less than 70 psi under distillation conditions wherein vapor phase and liquid phase are present:
  (i) contacting said streams in a distillation reaction zone with a hydrogenation catalyst prepared in a form to act as a distillation structure thereby to selectively hydrogenate a portion of said highly unsaturated compounds with said hydrogen to form less unsaturated hydrocarbons in a reaction mixture in a mixed vapor/liquid phase, and
  (ii) separating olefins produced by said selective hydrogenation from said reaction mixture by fractional distillation in said distillation structure while providing for condensing of a portion of said hydrocarbons comprising said olefins and highly unsaturated hydrocarbon compounds.

65. The process according to claim 64 wherein said hydrocarbon stream comprises aliphatic compounds having three to nine carbon atoms.

66. The process according to claim 64 wherein said hydrocarbon stream comprises a major amount of normal olefins which are recovered as products from said hydrogenation.

67. The process according to claim 64 wherein said hydrocarbon has a, WHSV in the range of 0.1 to 35.

68. The process according to claim 65 wherein the overhead pressure is in the range of 0 to 350 psig.

69. The process according to claim 66 wherein the hydrogen partial pressure is less than 50 psia.

70. The process according to claim 69 wherein the hydrogen partial pressure is less than 10 psia.

71. The process according to claim 70 wherein the hydrogen partial pressure is less than 7 psia.

72. The process according to claim 68 wherein said hydrogen partial pressure is less than 50 psia.

73. The process according to claim 72 wherein the hydrogen partial pressure is less than 10 psia.

74. The process according to claim 73 wherein the hydrogen partial pressure is less than 7 psia.

75. The process according to claim 65 wherein hydrogenation catalyst comprises a Group VIII metal or metal compound as the principal catalytic component.

76. The process according to claim 75 wherein said catalyst comprises Pd.

77. The process according to claim 68 wherein said overhead pressure is in the range of 50 to 150 psia.

78. The process according to claim 76 wherein said catalyst contains silver.

\* \* \* \* \*